US011243312B2

United States Patent
Petrak

(10) Patent No.: US 11,243,312 B2
(45) Date of Patent: Feb. 8, 2022

(54) IMAGING DETECTOR SYSTEM FOR GAMMA RADIATION USING UNIDIRECTIONAL AND BIDIRECTIONAL COMPTON SCATTERING PROCESSES

(71) Applicant: Hellma Materials GmbH, Jena (DE)

(72) Inventor: Sibylle Petrak, Hena (DE)

(73) Assignee: Hellma Materials GmbH, Jena (DE)

( * ) Notice: Subject to any disclaimer, the term of this patent is extended or adjusted under 35 U.S.C. 154(b) by 0 days.

(21) Appl. No.: 17/101,468

(22) Filed: Nov. 23, 2020

(65) Prior Publication Data
US 2021/0239862 A1 Aug. 5, 2021

(30) Foreign Application Priority Data

Nov. 22, 2019 (DE) .................... 10 2019 131 695.2
Nov. 22, 2019 (DE) .................... 10 2019 131 696.0

(51) Int. Cl.
| | | |
|---|---|---|
| G01T 1/167 | (2006.01) |
| G01T 1/164 | (2006.01) |
| A61B 6/03 | (2006.01) |
| G01T 1/29 | (2006.01) |
| G06T 11/00 | (2006.01) |
| G01T 7/00 | (2006.01) |

(52) U.S. Cl.
CPC .............. *G01T 1/167* (2013.01); *A61B 6/037* (2013.01); *G01T 1/1642* (2013.01); *G01T 1/1644* (2013.01); *G01T 1/2985* (2013.01); *G06T 11/006* (2013.01); *G01T 7/00* (2013.01); *G06T 2211/421* (2013.01)

(58) Field of Classification Search
CPC ................................ G01T 1/167; A61B 6/037
See application file for complete search history.

(56) References Cited

U.S. PATENT DOCUMENTS

| | | |
|---|---|---|
| 2002/0011571 A1 | 1/2002 | Lin et al. |
| 2004/0251418 A1 | 12/2004 | Gunter |
| 2009/0256080 A1 | 10/2009 | DeVito |

*Primary Examiner* — Edwin C Gunberg
(74) *Attorney, Agent, or Firm* — Buchanan Ingersoll & Rooney PC

(57) ABSTRACT

A device for generating one or more images of a source distribution of a gamma radiation field in the near and far field can include a detector system that includes several synchronized detectors for detecting radiation, system electronics that registers coincidence events, a data acquisition system that stores the measurement data of the coincidence events, and an analysis unit that performs an image reconstruction, which reconstructs one or more images of the source distribution of the radiation field.

17 Claims, 21 Drawing Sheets

$$\sigma = \frac{E2 - E1}{E1 + E2}$$

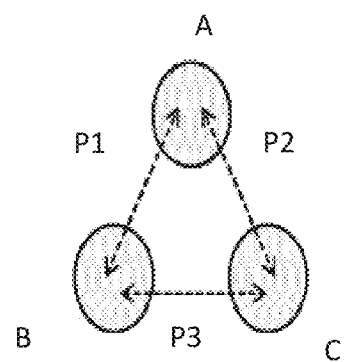
FIG. 5d
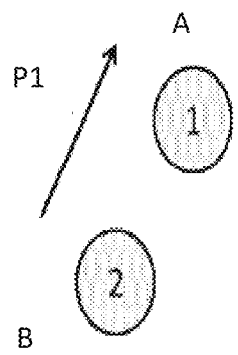
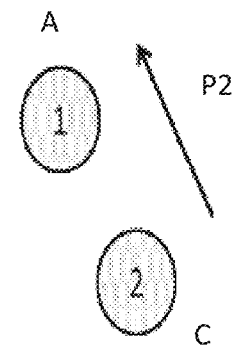
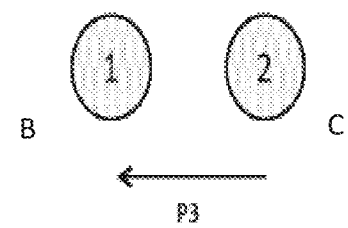
FIG. 5a
FIG. 5b
FIG. 5c

$$\sigma = \frac{E2 - E1}{E1 + E2}$$

| | P1 | P2 | P3 |
|---|---|---|---|
| -1,0 | 0 | 3 | 1 |
| -0,9 | 85 | 55 | 49 |
| -0,8 | 137 | 119 | 107 |
| -0,7 | 67 | 72 | 81 |
| -0,6 | 48 | 58 | 60 |
| -0,5 | 46 | 92 | 113 |
| -0,4 | 24 | 147 | 114 |
| -0,3 | 28 | 107 | 85 |
| -0,2 | 27 | 77 | 44 |
| -0,1 | 20 | 49 | 23 |
| 0,0 | 32 | 30 | 7 |
| +0,1 | 31 | 10 | 2 |
| +0,2 | 47 | 8 | 4 |
| +0,3 | 75 | 10 | 11 |
| +0,4 | 108 | 16 | 20 |
| +0,5 | 181 | 26 | 32 |
| +0,6 | 251 | 46 | 42 |
| +0,7 | 322 | 58 | 69 |
| +0,8 | 314 | 43 | 35 |
| +0,9 | 28 | 5 | 0 |
| +1,0 | | | |

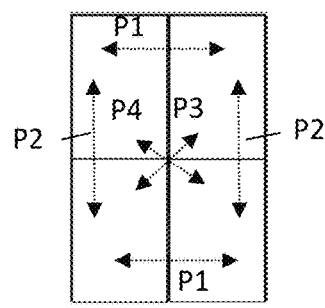
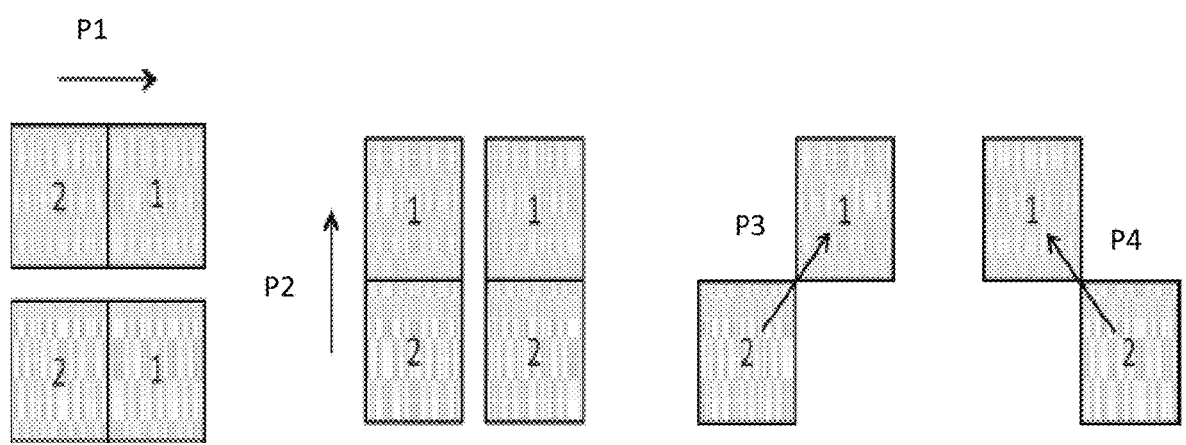
FIG. 7e
FIG. 7a  FIG. 7b  FIG. 7c  FIG. 7d $$\sigma = \frac{E2 - E1}{E1 + E2}$$

| | P1 | P2 | P3 | P4 |
|---|---|---|---|---|
| -1,0 | 4 | 8 | 10 | 23 |
| -0,9 | 7 | 5 | 19 | 57 |
| -0,8 | 14 | 11 | 47 | 33 |
| -0,7 | 53 | 72 | 52 | 68 |
| -0,6 | 41 | 58 | 60 | 71 |
| -0,5 | 27 | 62 | 75 | 80 |
| -0,4 | 38 | 78 | 114 | 66 |
| -0,3 | 54 | 98 | 128 | 53 |
| -0,2 | 66 | 77 | 148 | 58 |
| -0,1 | 78 | 63 | 167 | 42 |
| 0,0 | 125 | 121 | 170 | 31 |
| +0,1 | 136 | 288 | 152 | 29 |
| +0,2 | 121 | 301 | 121 | 16 |
| +0,3 | 134 | 450 | 110 | 22 |
| +0,4 | 159 | 476 | 104 | 17 |
| +0,5 | 211 | 387 | 94 | 28 |
| +0,6 | 331 | 322 | 87 | 36 |
| +0,7 | 371 | 239 | 69 | 74 |
| +0,8 | 414 | 164 | 35 | 18 |
| +0,9 | 254 | 53 | 32 | 85 |
| +1,0 | | | | |

2-plane Compton camera
Additional detector pairs in a Type A separated detector system
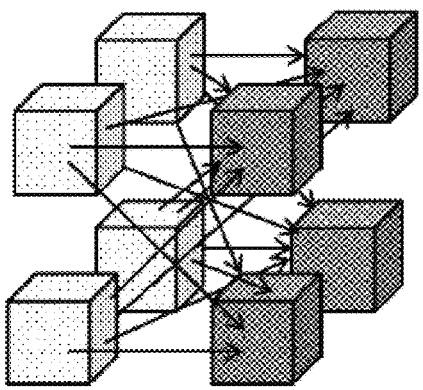
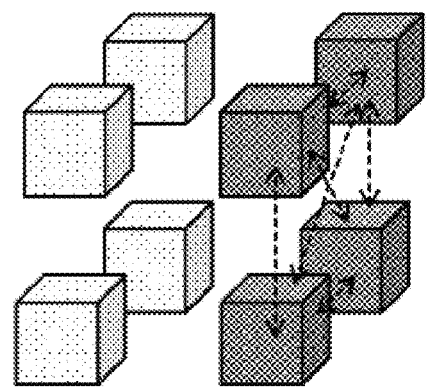
FIG. 9a PRIOR ART
FIG. 9b

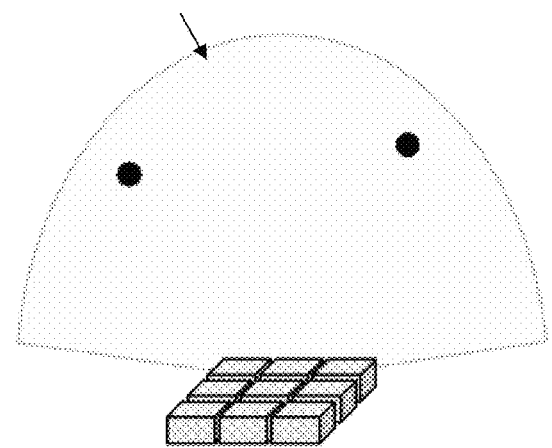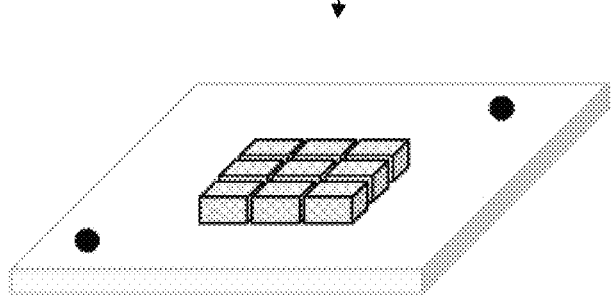
For hemispherical images of radiation source (Type A)
For images of radiation sources in the detector plane (Type B)
Fig. 10a
Fig. 10b

Type A

Type B

Fig. 12a
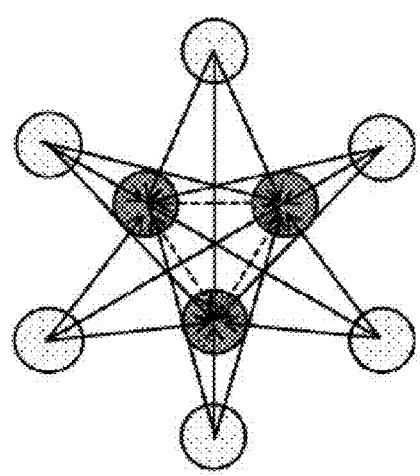
Fig. 12b
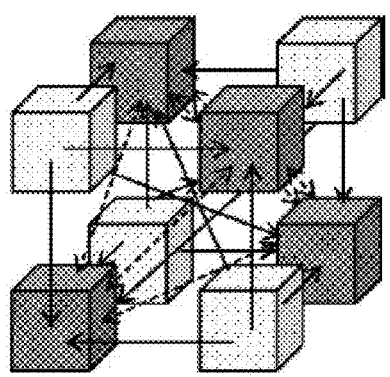
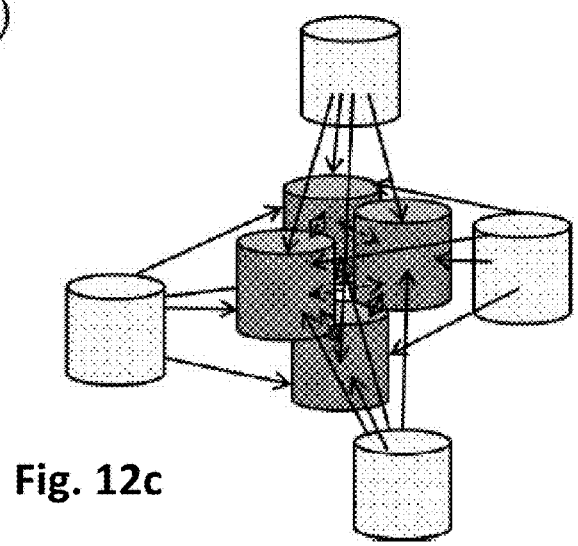
Fig. 12c

Further variant of type B detector system

Further variant of type B detector system

IMAGING DETECTOR SYSTEM FOR GAMMA RADIATION USING UNIDIRECTIONAL AND BIDIRECTIONAL COMPTON SCATTERING PROCESSES

CROSS-REFERENCE TO RELATED APPLICATIONS

The present application claims priority to German Patent Application Nos. 10 2019 131 696.0 and 10 2019 131 695.2. The entirety of these German patent applications are incorporated by reference herein.

FIELD

The invention relates to a system as well as to a method of radiation detection, in particular, to an imaging detector system for generating tomographic sectional images of activity distributions and for measuring the direction of radiation sources. The system and method are applicable in the near field and the far field of a source volume from which the radiation is emitted. In particular, activity distributions of radiopharmaceuticals can be detected in a patient. Embodiments of the system according to the invention also enables the detection of gamma radiation sources in the field by emergency forces of the ABC and radiation protection, as well as the detection of gamma radiation sources of cosmic origin, as they may be observed in astronomy by means of gamma radiation telescopes.

BACKGROUND

In the field of radiation detection, frequently, the determination of the spatial distribution of an activity concentration in a source volume is of interest. According to the application area, the requirements of the measurement systems and methods are very different. However, the physical principles, which are used by the measurement systems may be identical.

A frequently used direction-dependent detection principle is Compton scattering of gamma radiation at an electron in the detector material. Corresponding devices and systems for this are referred to as Compton cameras or Compton telescopes.

Compton cameras and Compton telescopes are composed of arrangements of several radiation detectors. Coincidences of respectively two detectors are recorded, if both detectors simultaneously have an energy input. The coincidence method exploits the concurrence of two ionization processes, which emanate from the recoil electron and—spatially shifted thereto—from the scattered radiation, which is able to ionize a second detector.

Compton telescopes have been widespread use in gamma astronomy for the past 50 years. The first use of a Compton telescope goes back to Schönfelder [Nuclear Instruments & Methods 107 (1973) 385]. The success of this technology is demonstrated by the many balloon experiments and satellites, which have explored and still are exploring cosmic gamma radiation sources by means of Compton telescopes.

In 1974, Todd, Nightingale and Everett have proposed to employ Compton cameras in nuclear medicine [Nature 251 (1974) 5471]. In medical applications, a particular challenge is that the patient is present within a finite distance in front of or even in the Compton camera, which causes a parallax error and poses increased requirements to the image reconstruction.

In the clinical field, Compton cameras compete with SPECT (Single Photon Emission Computed Tomography) and PET (Positron Emission Tomography), which are the two most commonly used imaging techniques in nuclear medicine.

The advantages and disadvantages of SPECT and PET have been described in expert literature comprehensively, and will not be further discussed here. However, it is commonly acknowledged that a substantial limitation of SPECT is the very low detection efficiency due to the collimators. Moreover, there is a limitation in the energy range of SPECT scanners. Commonly, SPECT is used in conjunction with the radionuclide Tc-99m, the gamma energy of which is 141 keV. For high-energy nuclides, SPECT is not suitable. From a medical point of view, however, the energy range up to 640 keV is interesting. For the energy range above 200 keV, at present, there is no suitable emission tomograph for single photon gamma radiation available.

A third application area for Compton cameras is ABC and radiation protection. Here, the aim is to detect hidden or forbidden radioactive sources. Radiation sources are to be detected, in case, for example, larger infrastructural facilities, major events, movements of persons and goods at airports, borders, and train stations are monitored with respect to radiation sources. Safety specialists for ABC protection need devices, in order to localize hazardous radiological and nuclear substances.

At this point, a short overview of the designs for Compton cameras according to prior art is given. Known designs for Compton cameras either use a detector arrangement in two planes or in one plane.

With respect to the classical two-plane Compton design, the first plane consists of detectors of a material having a low atomic number Z, and the second one of detectors of a material having a high atomic number. The detectors of the first plane having a low Z have a high probability for Compton scattering for gamma energies from 100 keV to 3 MeV. Subsequently, the scattered gamma radiation falls onto the second plane, the detectors of which with a high Z have a high probability of absorbing radiation in this energy range. Both planes are spaced apart from each other at a distance of approximately 30 cm to 1 m.

A characteristic feature of the 2-plane Compton camera is that the detector electronics only processes and records such coincidence events, in which a detector having a low atomic number and a detector having a high atomic number are involved. Coincidences between two detectors having a low atomic number or between two detectors having a high atomic number are irrelevant for the classical 2-plane Compton camera.

US 2012/0114100 describes a measurement system having two radiation detectors and one coincidence circuit, which is suitable for measuring the direction of a radiation source. The two detectors may be substantially identical in design, or may also be different. In US 2012/0043467, a Compton camera is described, which uses a coplanar arrangement of radiation detectors for direction measurement. This Compton camera which is referred to as Single Plane is characterized by its simple and compact design.

The devices described in US 2012/0114100 and US 2012/0043467 are not dependent on detectors with a low atomic number. A subdivision of the detectors into scattering detector and absorption detector is not necessary for these devices. The Single Plane Compton camera in US 2012/0043467 allots a dual role to the detectors. Each detector in a Single Plane Compton camera is able to scatter the radiation as well as to absorb it. For this, the detector materials of medium to high Z are suitable, which have similar probabilities for Compton scattering and for photoelectric absorption in the energy range from 100 keV to 3 MeV.

SUMMARY

Embodiments of the imaging detector system according to the invention is a further development of the known designs for Compton cameras. The classical 2-plane Compton camera and the Single Plane Compton camera from US 2012/0043467 are identified as special cases of the imaging detector system according to the invention. Both designs—the 2-plane Compton camera and the Single Plane Compton Camera—are modified and improved by the invention. Moreover, the invention opens up new designs for Compton cameras, which have not yet been known.

In US 2012/0114100 and US 2012/0043467, methods for direction measurement are also described. These methods are adapted to determine the direction of a radiation source. It is required that there is one radiation source at maximum for each nuclide. All rays of a nuclide have to be incident on the system at an angle. The incidence angle may then be determined for 2-dimensional and 3-dimensional measurement situations.

According to US 2012/0114100 and US 2012/0043467, the direction measurement is explained, as follows: the energies measured in coincidence events in respectively two radiation detectors are acquired in two separate spectra. Subsequently, the energy mean values of both spectra are calculated. The direction of incidence may be determined based on an empirical relation, which expresses the direction as a function of the mean energy values.

The methods of US 2012/0114100 and US 2012/0043467 are the first methods for direction measurement by means of a Compton camera, according to which the scattering and absorption detectors do not have to be distinguishable physically. A substantial limitation of the methods, however, results from their restriction to a single source per nuclide, because only the energy mean values of both detectors are taken into consideration. If several radiation sources of the same nuclide are present, the methods cannot be applied. The methods described are not suitable for imaging. They are limited to the direction measurement of a radiation source.

It is an object of the invention to provide an imaging detector system for gamma radiation, which overcomes the disadvantages of the prior art. The system should be applicable to astronomy, medicine, and in ABC and radiation protection, and should meet the specific requirements of the devices in these technical fields.

In astronomy, high performance highly sensitive Compton telescopes are in demand. One of the requirements in medical engineering is a substantial improvement of the detection efficiency of SPECT scanners, and an extension of the application area to high-energy nuclides to an energy of 640 keV. With respect to ABC and radiation protection, compact devices are required, which are able to measure a direction distribution of a radiation field in real-time and by using only few radiation detectors.

These objects are solved according to the invention by embodiments of an imaging detector system and methods of making and using such a system.

The imaging detector system for gamma radiation in the near and far field according to an exemplary embodiment of the invention can include a group of several synchronized detectors for the detection of radiation. Hereby, at least one detector material has an atomic number of $Z_{eff}>30$. All detectors of the imaging detector system according to the invention measure the energies E and the interaction points $\underline{d}$, which occur in interactions of the radiation with the detector materials. The detector materials, thereby, are segmented virtually and physically into voxel.

The smallest distinguishable volume units of the detector materials are referred to as voxel or detector voxel. A particular voxel is identified by the x, y, and z coordinates of its spatial center $\underline{d}$.

Further, the imaging detector system according to embodiments of the invention can include a system electronics, which registers coincidence events, if interactions occur simultaneously been two detector voxel from a list of defined voxel pairs, respectively. The list of defined voxel pairs comprises all pairs, which may be created in combination from the set of all detector voxels, wherein the defined voxel pairs comprise at least one detector voxel from a material having an atomic number of $Z_{eff}>30$.

Further, embodiments of the imaging detector system can include a data acquisition system, which stores the measurement data of the coincidence events. For both detector voxels involved in a coincidence event, a ranking is set, which defines a first and a second detector voxel. In each defined voxel pair, the voxel having the lower atomic number receives the number 1, and that one having the higher atomic number, the number 2. If both detector voxels of a pair should have the same atomic number, the identification as 1 or 2 is chosen arbitrarily. The energies ($E_1$, $E_2$) and the interaction points ($\underline{d}_1$, $\underline{d}_2$) measured in coincidence events are sorted corresponding to their identification 1, 2, and are stored in a chronological list together with the attributes $\underline{y}=\{\underline{d}_1, E_1, \underline{d}_2, E_2\}$ and the detector time t.

Moreover, embodiments of the imaging detector system can include an analysis unit, which is connected to the data acquisition system, and which generates projection data $\underline{p}(\underline{y})$ from the stored measurement data, which is defined as a function of the attributes $\underline{y}=\{\underline{d}_1, E_1, \underline{d}_2, E_2\}$, wherein a function $\sigma(E_1, E_2)$ is applied, which is traceable to a function $\sigma(E_1)$ when substituting $E_2$ by $C-E_1$, which is clearly defined, constant, and monotonous over the entire interval [0, C], and wherein C is a constant, which represents the radiation energy $C=E_1+E_2$. Die analysis unit performs an image reconstruction, which reconstructs one or more images $\underline{f}(\underline{x})$ of the radiation field from the projection data $\underline{p}(\underline{y})$.

Further, also embodiments of a method of detecting and imaging gamma radiation is subject-matter of the invention. The imaging detector system can facilitate imaging activity and direction distributions of radiation fields emitting gamma radiation. It may be applied for the near and the far field. Embodiments of the method can facilitate detecting and imaging gamma radiation by using an embodiment of the imaging detector system.

Embodiments of the method can include the detector materials being segmented virtually or physically into voxels, wherein the method uses unidirectional or bidirectional Compton scattering processes and comprises a system matrix $\underline{H}$, a defined functional value $\sigma(E_1, E_2)$ and a list of defined voxel pairs, and is adapted for the acquisition of projection data $\underline{p}(\underline{y})$ of the measurement values and for the calculation of the image data $\underline{f}(\underline{x})$.

Thereby, the method can include:
  creating a list of defined voxel pairs, wherein the defined voxel pairs comprise all pairs, which may be formed from the quantity of detector voxels, and wherein each pair comprises at least one detector voxel from a material having an atomic number of $Z_{eff} > 30$;

interconnecting all detectors/voxels in a coincidence circuit such that coincidence events are detected in all defined voxel pairs;

identifying the two detector voxels of each voxel pair with the numbers 1 and 2, respectively, wherein the detector voxel having the lower atomic number receives the number 1, and that one having the higher atomic number the number 2, wherein in case both detector voxels consist of the same material, the identification is made arbitrarily;

defining a function $\sigma(E_1, E_2)$, which is calculated from two energy values $E_1$ and $E_2$, wherein such functions $\sigma(E_1, E_2)$ are allowed, which are traceable to a function $\sigma(E_1)$ when substituting $E_2$ by $C-E_1$, which are clearly defined, constant and monotonous over the entire interval $[0, C]$, wherein C is a constant, which represents the radiation energy $C=E_1+E_2$;

acquiring measurement values $\underline{y}=\{\underline{d}_1, E_1, \underline{d}_2, E_2\}$ of coincidence events, if interactions take place simultaneously in respectively two detector voxels of all defined voxel pairs, wherein the measurement values originate from a radiation near or far field, and the measurement values are the energies $(E_1, E_2)$ measured in the detector voxels and the interaction points $(\underline{d}_1, \underline{d}_2)$, associating coincidence events $\underline{y}=\{\underline{d}_1, E_1, \underline{d}_2, E_2\}$ with a first detector voxel/detection location $\underline{d}_1$ and a second detector voxel/detection location d;

calculating the functional value $\sigma(E_1, E_2)$ from two energy values $(E_1, E_2)$ per coincidence event;

acquiring the coincidence events corresponding to their first detector voxel $\underline{d}_1$, their second detector voxel $\underline{d}_2$ and their $\sigma(E_1, E_2)$ value in an element of the projection data $\underline{p}(\underline{y})$, wherein separate projection data $\underline{p}(\underline{y})$ are acquired for each radio nuclide;

calculating one or more images $\underline{f}(\underline{x})$ from the projection data $\underline{p}(\underline{y})$ by means of a statistical imaging reconstruction method of emission tomography using the system matrix $\underline{H}$, wherein for each radio nuclide, a separate image $\underline{f}(\underline{x})$ is calculated; wherein the images $\underline{f}(\underline{x})$ represent an activity distribution in a source volume or a flux density distribution across the incident directions.

Within the meaning of the invention, the geometrical near and far fields are considered as near and far fields. A near field is present, if the imaging detector system is located close to a source volume, i. e., if at least one radiation source is located that close to the detector system that its distance is estimated to be finite with respect to the dimensions of the detector system. In a far field, all radiation sources are located that far from the detector system that their distances are much larger than the detector system. The far field, thereby, is characterized in that no parallax error occurs. For the image reconstruction, it is important that a far field does not have a radial dependence and is only dependent on the direction of incidence. In the far field, the contributions of individual sources along one direction are not distinguishable; the overall intensity of the radiation can be measured from one direction only.

Unless otherwise stated, for all use cases of the detector system according to the present invention, in nuclear medicine, the requirements of the near field are considered as being suitable within the meaning of the invention. All use cases of the detector system according to the invention, in astronomy or in ABC and radiation protection are covered by the requirements of the far field, as far as not otherwise specified.

The imaging detector system can also include a group of several synchronized radiation detectors, which may be available in an arbitrary linear, planar or spatial arrangement. Also, detector segments are considered as radiation detectors within the meaning of the invention, if they can be read out individually. Thereby, at least one radiation detector has a medium to high atomic number Z.

As medium atomic number, a number larger than 30 or smaller than 50 is concerned within the meaning of the invention. A number larger than 50 is considered to be a high atomic number within the meaning of the invention. If the detector materials are present as chemical compounds, then Z is considered to be the effective atomic number $Z_{eff}$, i. e., the mean atomic number of all elements in the compound under consideration of the atomic masses of the elements and their stoichiometric composition.

The detector system can obtain its imaging properties by the selection of suitable detector pairs from the group of synchronized radiation detectors. As far as not otherwise described, a detector is considered as a radiation detector within the meaning of the invention. A suitable detector pair comprises at least one detector from a material of medium to high atomic number, that means, every selected detector pair has at least one detector with an atomic number $Z_{eff}$ higher than 30.

For setting up of the imaging detector system, a maximum of pair combinations of radiation detectors has to be considered, i. e., an attempt is made to preferably use each combination of radiation detectors, which is reasonable for the respective application. By using as many of these combinations as possible, an efficient imaging may be effected under optimal conditions for the subsequent image reconstruction.

Both radiation detectors of each detector pair can be indicated uniquely by the numbers 1 and 2, respectively. The detector pair having the lower atomic number receives the number 1; that one having a higher atomic number receives the number 2. If both detectors consist of the same material, the indication as 1 and 2, respectively, is selected arbitrarily, as far as it is maintained consistently.

The indication of the detectors for each selected detector pair as first and second detector, respectively, is necessary for the image reconstruction method belonging to the invention, but moreover, it does not imply necessarily, how the process actually has taken place. Within the meaning of the invention, the indications first and second detectors are not to be understood such that the ionization process, which has triggered the (nearly) simultaneous ionization of both detectors of the pair has necessarily started in the first detector and has ended in the second detector. This interpretation, which is of substantial relevance for the classical 2-plane Compton camera, may be correct for the detector system according to the invention, however, does not necessarily have to be correct. Basically, the indications first and second detector are to be understood only as an indication necessary for the image reconstruction. Indication is of geometric, relevance, because it defines a direction within the space.

With respect to the classical 2-plane Compton camera, each detector may be clearly identified according to its atomic number $Z_{eff}$ as scattering or absorption detector. Detectors from materials with $Z_{eff} \leq 30$ are scattering detectors, detectors from materials with $Z_{eff} > 30$ are absorption detectors.

The imaging detector system according to the invention does not necessarily comprise such a functional separation. The roles, which the scattering and absorption detectors usually take in the classical 2-plane Compton camera, are carried out by a first and a second radiation detector in the imaging detector system according to the invention, in correspondence with the definition according to the invention how the detectors are to be numbered in a detector pair.

Those detector pairs of the imaging detector system, which comprise a detector from a material having an atomic number of $Z_{eff} \leq 30$ and a second detector from a material of $Z_{eff} > 30$ are referred to as unidirectional. For the unidirectional detector pairs, the physical functional assignment known from the classical 2-plane Compton camera is applicable: the detector having the no. 1 is the scattering detector, and that one having the no. 2 is the absorption detector.

All other selected detector pairs of the imaging detector system that are not unidirectional, are referred to as bidirectional. With respect to the direction or detection processes, it is not possible to determine, in which sequence the interactions have taken place in a coincidence event. As far as no other information is available, in such detector pairs, it is not possible to identify, which detector scatters the radiation in a coincidence event, and which one has absorbed it. The reaction may have taken place in both directions—from 1 to 2 or from 2 to 1, its direction remains unknown. With respect to the bidirectional detector pairs, the indication of the detectors as first and second detector is only of geometrical relevance. A physical statement with respect to the direction of the scattered radiation is not possible for bidirectional detector pairs.

Further, the detector system can also include detector electronics, which registers signals from the radiation detectors and determines their information concerning the absorbed radiation energy. Each detector of the detector system according to the invention is calibrated for an energy measurement.

The detector system can also include a system electronics for synchronization of the signals from the individual radiation detectors and for recognition and storage of coincidence events in form of a chronological list. The system electronics identifies coincidence events from two signals occurring simultaneously in the selected detector pairs, and transmits this information to the data analysis. For each coincidence event, a vector $\underline{y}$ is defined, which contains all information concerning the coincidence, i. e., the interaction points ($\underline{d}_1$, $\underline{d}_2$) and the energies ($E_1$, $E_2$) of both interactions in the detectors 1 and 2:

$$\underline{y} = \{\underline{d}_1, E_1, \underline{d}_2, E_2\} \qquad (6)$$

A suitable form of data storage is the data acquisition in form of a chronological list in a so-called list mode. Each coincidence event is stored together with the measurement values $\underline{y}$ mentioned in eq. (1) and the detection time t.

According to an embodiment of the imaging detector system according to the invention, the interaction points ($\underline{d}_1$, $\underline{d}_2$) are measured with a suitable device comprised in the system. In the field of detector design, various possibilities for radiation detection with spatial resolution are known. These include, for example, modules of pixelated radiation detectors. Other designs use segmented semiconductor detectors. For scintillation detectors, also, various techniques for radiation detection with spatial resolution are known. A detector system referred to as temporal imaging is described in U.S. Pat. No. 9,638,811 B2. Specialists for this technical field are readily able to design a detector system with spatial resolution, which is able to determine the interaction points ($\underline{d}_1$, $\underline{d}_2$).

In a further embodiment of the imaging detector system according to the invention, the interaction points are not measured individually for each interaction, but rather are approximated based on the spatial location of the radiation detector. This embodiment applies for detector systems, which are composed of detectors, which are only able to determine the energy, but however, are not able to determine the interaction point. In this embodiment, the interaction point of an event registered in the detector is equated with the spatial center of the active detector medium.

As the projection data $p(\underline{y})$ of the imaging detector system, the number of coincidence events is concerned, which have the same vector $\underline{y}$ for the measured attributes $\{\underline{d}_1, E_1, \underline{d}_2, E_2\}$. The projection data $p(\underline{y})$ are generated from the interaction of the radiation and the imaging detector system.

An analysis unit, which processes all coincidence events, which are present in the chronological list, and generates the projection data $p(\underline{y})$ from these can also be included in the detector system. The detector system can be configured to utilize all entries of the coincidence events in the chronological list for the image reconstruction. Only such entries are excluded, which originated from pairs, in which both detectors have a low atomic number of $Z_{eff} \leq 30$, and neither one of the detectors has a sufficient probability for the photoelectric effect.

The analysis unit has the task k to reconstruct an image of the radiation distribution ($\underline{y}$) from the protection data. The image reconstruction, thereby, can be carried out as follows in some embodiments:

According to an embodiment of the imaging detector system according to the invention, the detector system is located in the near field of a source volume, from which the radiation is emitted. If $\underline{x}$ is a point in the source volume, the activity density $f(\underline{x})$ is considered as being the number of gamma photons per time unit emitted at the point $\underline{x}$. The task of the image reconstruction is to reconstruct the activity density $f(\underline{x})$ from the projection data ($\underline{y}$), which is recorded by the imaging detector system.

In another embodiment, the imaging detector system according to the invention is located in the far field of a source volume. In this embodiment, $\underline{x}$ describes the incidence direction, in which the radiation emitted from the source volume is received by the detector system. In this embodiment, the function $f(\underline{x})$ describes a flux density, i. e. the number of gamma photons, which arrive at the detector system from the direction $\underline{x}$ per spatial angle and per time unit. According to this variant of an embodiment, the image reconstruction is responsible for reconstructing the flux density $f(\underline{x})$ from the projection data $p(\underline{y})$. For tasks of the ABC and radiation protection, the flux density $f(\underline{x})$ may be calibrated as dose rate density within the context of a use of the imaging detector system according to the invention.

The function $f(\underline{x})$ is also referred to as an image within the meaning of the invention. According to the application, the image $f(\underline{x})$ may represent an activity density, a flux density, and a dose rate density, respectively. The procedure for generating a picture $f(\underline{x})$ from the projection data $p(\underline{y})$ also is referred to as rear projection and deconvolution, respectively. The inverse procedure, according to which an illustration of the projection data $p(\underline{y})$ is generated from an image $f(\underline{x})$, is denoted as forward projection.

The analysis unit belonging to the imaging detector system according to the invention performs the image reconstruction by means of a statistical or iterative image reconstruction method. Such image reconstruction methods, predominantly, have been developed for clinical applications in emission tomography. For example, the Maximum Likelihood Maximization Method (MLEM) of Shepp and Vardi [IEEE Transactions on Medical Imaging 1 (1982) 113] belongs to the statistical image reconstruction methods. A large number of these methods is free for use without any limitations, and its implementation is well known to the specialists in this technical field.

The statistical image reconstruction methods have the advantage that they may be applied for any arbitrary imaging detector systems, which are available for gamma radiation, with minor modifications. Statistical image reconstruction methods are universally applicable. They are applicable for PET and SPECT scanners, for Compton cameras, and for the imaging detector system according to the invention. Their application area is not limited to a certain functional principle, on which the detection process is based. The statistical methods support the image reconstruction for gamma radiation from the near field and the far field and for all radio isotopes.

The statistical image reconstruction methods discretize the image and detector space into voxels and pixels, respectively.

According to the embodiment of the invention for the near field, the three-dimensional image space is subdivided into voxels. According to the embodiment for the far field, the image space is two-dimensional and represents a spherical surface. The spherical surface is subdivided into pixels of equal surface area. The statistical image reconstruction methods calculate the pixel values of the flux density on a spherical surface. A frequently used projection for illustrating a spherical surface in a plane, for example, is the Mollweide projection, which also is known as Babinet projection. In this embodiment of the invention, the flux density is displayed as elliptical face.

If the image and detector space is subdivided into voxels and pixels, respectively, the following vector equation this applicable:

$$\underline{p} = \underline{H}\underline{f}^T \tag{7}$$

Eq. (2) defines a functional relationship between the projection data $p(\underline{y})$ that now is discrete, and the discrete image data $\underline{f}(\underline{x})$. $\underline{p}$ and $\underline{f}$ now are vectors, the elements of which $p_i$ and $f_j$ represent the values of the $i^{th}$ and $j^{th}$ sites in the respective vector spaces. The matrix $\underline{H}$ usually is referred to as projection and as system matrix, respectively. The elements $H_{ij}$ of the system matrix $\underline{H}$ have different meanings in the near field and far field. In the near field, the elements $H_{ij}$ represent the probabilities that a gamma quantum emitted in the voxel j triggers a coincidence event, which symbolically is referred to as i. In the far field, the elements $H_{ij}$ represent the probabilities that a gamma quantum that is incident from the direction j triggers a coincidence event i. Both forms have in common that the system matrix $\underline{H}$ describes all physical relationships, which characterize the detector system, including the characteristics of the radiation detectors and the influence of the electronics. Basically, there are three approaches for creating the system matrix $\underline{H}$: this may be created directly by measurements by means of the detector system and by means of Monte Carlo simulations, respectively, or by means of a theoretical model.

The discrete approach to subdivide an image and detector space into voxels and pixels, respectively, on which all statistical image reconstruction methods are based, simplifies the image reconstruction, and is particularly suitable for such embodiments of the invention, in which the measurement data is available in discrete form anyways, as e. g., with respect to pixelated or segmented radiation detectors.

There is a number of embodiments of the invention, how the detector space may be discretized. According to an embodiment of the invention, the detector system is composed of detectors, which do not provide location information. In this embodiment, each radiation detector may be considered as discrete unit. Each element of $\underline{p}$ consists of a number of coincidence events, which are registered with respect to a respective combination of a particular first detector with a particular second detector at a particular functional value $\sigma(E_1, E_2)$. The functional value $\sigma(E_1, E_2)$ represents the direction information comprised in the energy values $E_1$ and $E_2$.

In a classical 2-plane Compton camera, the functional value typically is defined as Compton scattering angle $\theta$ $$\vartheta = \cos^{-1}\left(1 - \frac{mc^2}{E_2} + \frac{mc^2}{E_1 + E_2}\right) \tag{8}$$

with $mc^2 = 511$ keV, the rest energy of the electron. However, this definition is only reasonable, if it is assumed that the radiation has been scattered in detector 1 and has been absorbed in detector 2. In the imaging detector system according to the invention it is, however, not known at all, where the radiation has been scattered and where it has been absorbed.

The analysis unit of the imaging detector system according to the invention uses a function $\sigma(E_1, E_2)$, which has to be clearly defined for all energy values $0 \leq E_1 \leq C$ and $0 \leq E_2 \leq C$. Hereby, C represents the radiation energy $C = E_1 + E_2$. The applicability of a particular function $\sigma(E_1, E_2)$ may be determined by replacing the variable $E_2$ by $C - E_1$. If the thus gained function $\sigma(E_1)$ is clearly defined, constant and monotonous over the entire interval $0 \leq E_1 \leq C$, the function $\sigma(E_1, E_2)$ is an allowable function within the meaning of the invention.

A suitable definition for the functional value $\sigma$ according to this invention is:

$$\sigma(E_1, E_2) = \frac{E_2 - E_1}{E_1 + E_2} \tag{9}$$

In Eq. (4), the index 1 refers to the energy $E_1$ measured in detector 1, and the index 2 refers to the energy $E_2$ measured in detector 2, according to the previously set definition for numbering the detectors. The definition given in eq. (4) for the functional value $\sigma$ represents an embodiment of the invention; however, the invention is not limited to this; alternative definitions for $\sigma$ are covered by the invention.

According to an embodiment of the invention, the detector system is composed of molecules of pixelated radiation detectors having a medium to high atomic number. In this embodiment, each element of $\underline{p}$ consists of a number of coincidence events, which are counted for the respective combination of a particular first detector bin with a particular second detector bin for a particular functional value $\sigma(E_1, E_2)$. The vector space of $\underline{p}$ extends over all combinations of respectively two detector bins within a module, and over all combinations of each detector bin in a module with every detector bin in each other module. For each combination of respectively two detector bins, it has to be set unambiguously, which bin has the number 1 and which bin has the number 2. Moreover, the elements of p further are differentiated according to classes in the functional value $\sigma(E_1, E_2)$. The functional value $\sigma$ may be calculated according to eq. (4), or may be calculated otherwise.

According to an embodiment, the detector system with modules of pixelated radiation detectors of medium to high atomic number is used for a measurement in the far field. In this embodiment, the dimensionality of the vector p may be reduced by aggregating all elements of p, for which the first and the second detector bin respectively has the same distance and the same direction, and for which the functional values $\sigma(E_1, E_2)$ are matching.

According to a further embodiment of the invention, the detector system is composed of radiation detectors of medium to high atomic numbers, which use the temporal imaging function principle of U.S. Pat. No. 9,638,811 B2. According to U.S. Pat. No. 9,638,811 B2, the detector system is suitable for fast scintillation materials with pulse rise times less than a nanosecond. Here, it is assumed that all technical requirements according to U.S. Pat. No. 9,638,811 B2 are available. According to the invention, each radiation detector comprised in the system is subdivided virtually into discrete voxels. The elements of p are the numbers of coincidence events, which are counted for a respective combination of a particular first box and with a particular second voxel for a particular functional value $\sigma(E_1, E_2)$. The vector space of p extends over all combinations of one voxel in a radiation detector with each voxel in any other detector. For each combination of respectively two voxels, it is to be set unambiguously, which voxel has the number 1 and which voxel has the number 2. Further, the elements of p are also differentiated according to classes in the functional value $\sigma(E_1, E_2)$. The functional value $\sigma$ may be calculated according to eq. (4), or may be calculated otherwise.

If the technique disclosed in U.S. Pat. No. 9,638,811 B2 allows to measure the energies $E_1$ and $E_2$ of two interactions occurring simultaneously in a radiation detector separately, the vector space of p is extended correspondingly such that additionally, also all combinations of respectively two voxels within each radiation detector may be acquired.

In the following, it is assumed that the projection data p(y) of the detector system according to the invention is present as a vector. The image space for f(x) also this discretized, i. e., it is separated into voxels or pixels. The statistical image reconstruction methods, which according to the invention belong to the analysis unit, use eq. (2), in order to determine the values $f_j$ of the image vector f.

According to an embodiment of the invention, Expectation Maximization Algorithms (EM) are used as statistical image reconstruction methods in the analysis unit. EM image reconstruction methods belong to the most successful methods in emission tomography. These methods try to reach an acceptable solution for f by a sequence of approximations. Starting from a first estimation, it is tried to reconstruct the best approximation to the rear image f in a sequence of consecutively better estimations. In each iteration step, the present image f is used in order to generate a new image of the projection data by means of forward projection. The calculated projection data is compared to the measured data p. After a couple of iterations, the method converges to increasingly better matching the projection data calculated from f and the measurement data p. In the end, the method results in the image f, which is the highest probability for the observed distribution p.

According to an embodiment of the invention, the Maximum Likelihood Expectation Maximization method (MLEM) is used in the analysis unit, in order to calculate an image f from the projection data p of the detector system. The method applies the iteration procedure $$f_j^{[n+1]} = \frac{f_j^{[n]}}{\sum\limits_i^N H_{ij}} \sum_i^N \frac{p_i H_{ij}}{\sum\limits_l H_{il} f_l^{[n]}} \tag{10}$$

and calculates the image sequence $f^{[n]}$. With each iteration step n a new representation $f^{[n+1]}$ is calculated from the present representation $f^{[n]}$. The method begins with an initial distribution $f^{[0]}$.

According to an embodiment of the invention, the gamma radiation originates from several radio nuclides. Then, the imaging detector system according to the invention uses an analysis unit, which reconstructs a separate image for each radio nuclide. For this, the analysis unit sorts the coincidence events stored in the chronological list according to their energy sum $E_1+E_2$. Selection conditions are applied to the energy sum $E_1+E_2$, which correspond to the characteristic nuclide energies, the radiation of which is detected. For each radio nuclide, separate nuclide specific projection data p(y) is generated. The analysis unit registers only such coincidence events in the nuclide specific projection data p(y), the energy sum of which $E_1+E_2$ lies within a predefined range around the energy value of the respective nuclide energy. By means of such selection conditions, it is possible to analyze separate projection data p(y) for each detected nuclide. Moreover, events are sorted out, which do not correspond to the detection provided from a coincidence of a Compton scattering and a photoelectric absorption, because for example, there are two Compton scatterings, without a photoelectric absorption have taken place.

If the gamma radiation is emitted from a radio nuclide, which emits on several gamma lines, it is up to the user, whether the coincidence events are to be acquired in a uniform projection data set. For example, Co-60 has two gamma lines that are close to each other at 1173 keV and 1332 keV. Coincidence events of both emissions may be acquired without any problems in the same projection data set. Because those gamma energies are lying close to each other, also, the projection data sets are similar and may be analyzed together without any difficulties. If, however, a nuclide has several gamma lines that are located far away from each other, it is recommended to acquire these separately. In this case, several projection data sets are created, which will be merged later on in the image reconstruction program.

According to an embodiment of the invention, the analysis unit calculates, by means of the Maximum Likelihood Expectation Maximization Method (MLEM) according to eq. (5), a separate nuclide specific image f for each nuclide specific projection data set p. It is assumed that all required system matrixes H are available for the radio nuclides concerned.

The imaging properties of the imaging detector system according to the invention are determined by the material composition, the system electronics, and the spatial arrangement of the detector system. These relationships are applicable universally, and will be explained in more detail here.

According to an embodiment of the imaging detector system according to the invention, detector pairs are selected, which may be formed in combination from the quantity of all detectors, wherein the selected detector pairs comprise at least one detector of medium to high atomic number $Z_{eff}>30$. As many detector pairs as possible are selected, as it is reasonable for an application case. Further, as material for the radiation detectors with $Z_{eff}>30$, a pure or a doped scintillation material may be used, as NaI, CeBr$_3$, LaBr$_3$, LaCl$_3$, La(Br$_x$Cl$_{1-x}$)$_3$, CsI, SrI$_2$, BaF$_2$, CLYC, CLBC, CLCB, CLLB, BGO, LSO, LYSO, GAGG, YAP, YAG and/or a semiconductor material, as Ge, GaAs, CdTe and/or CdZnTe.

According to an embodiment of the imaging detector system according to the invention, the detector pairs are formed unidirectionally, such a unidirectional detector pair comprises a detector of lower atomic number $Z_{eff}\leq30$ and a detector of medium to high atomic number $Z_{eff}>30$. Further, as material for the radio detectors with $Z_{eff}\leq30$, a scintillation material may be used, as PVT, anthracene, stilbene, p-terphenyl, CaF$_2$, an organic liquid scintillator, and/or a semiconductor material, as Si.

According to a further embodiment of the imaging detector system according to the invention, the detector pairs are formed bidirectionally, such a bidirectional detector pair comprises two detectors of medium to higher atomic number $Z_{eff}>30$.

According to a further embodiment of the imaging detector system according to the invention, the detector pairs are formed unidirectionally as well as bidirectionally.

According to an embodiment of the imaging detector system according to the invention, the detector system is equipped with detector and system electronics, which analyzes the detector signals. The signals are analyzed with respect to their energies (discriminated) and with respect to their time structure (coincidence analysis). The energy discrimination and the coincidence analysis may be done by means of analog and/or digital electronics. Further, the analog electronics may comprise a combination of several types of modules, which in interconnection allow for an energy discrimination and a coincidence analysis of the signals. Further, a high-voltage supply, a preamplifier, an amplifier, a pulse former, a charge integrator, a pulse height analyzer, a multichannel analyzer (MCA), and/or a coincidence circuit may be used as electronic modules. Further, the digital electronics consists of hardware and software components, which digitalize, process, and store the signals of all radiation detectors, in order to carry out an energy discrimination and a coincidence analysis by means of digital means subsequently. Further, a high-voltage supply, and A/D converter per radiation detector, a Field Programmable Gate Array (FPGA), a storage medium, and/or a digital signal processor belong to the hardware of the digital electronics. Further, the digital electronics comprises a software for the digital signal and coincidence analysis, which analyzes the complete data set fully automatically in a multistage process. Further, the multistage analysis process is comprised of the digital signal and coincidence analysis together with the reading of data, the determination of essential signal properties, a digital signal filtering, the integration of signal paths, an energy standardization, a coincidence analysis, and the output of discrimination and coincidence information.

According to an embodiment of the imaging detector system according to the invention, the system electronics records the data of coincidence events as a chronological list. For each coincidence event occurring in a selected detector pair, the interaction points ($\underline{d}_1$, $\underline{d}_2$) and the energies ($E_1$, $E_2$) of the two interactions, including the detection time t are stored.

According to an embodiment of the imaging detector system according to the invention, all radiation detectors basically have the same design. However, it may also be provided for two of the radiation detectors having a design different to each other.

According to an embodiment of the imaging detector system according to the invention, the detector system is formed by a group of similar detectors, all detectors consist of materials of medium to high atomic number $Z_{eff}>30$ and have significant probabilities for photoelectric absorption as well as for Compton scattering in the energy range from 100 keV to 3 MeV. The materials may be similar or different. All detectors are arranged in a one layer homogeneous plane, wherein the plane may be plane or curved. Further, each detector may be combined to a pair with any other. The detector pairs are bidirectional, i. e., the radiation is scattered in both directions with similar intensity. Such a detector system is referred to as type B within the meaning of the invention.

According to a further embodiment of the imaging detector system according to the invention, the detector system is formed by detectors which may be subdivided into two groups. One group consists of detectors with materials of medium to high atomic number $Z_{eff}>30$, they have a high probability for photoelectric absorption in the energy range from 100 keV to 3 MeV. A second group consists of detectors with materials of lower atomic number $Z_{eff}\leq30$, they have high probabilities for Compton scattering in the energy range from 100 keV to 3 MeV. Detectors from one group are combined with detectors from the other group into pairs, these detector pairs are unidirectional, that means, the radiation is predominantly scattered in one direction, namely, from the detector having a lower atomic number to the detector having a medium or high atomic number. Additionally, the detectors of the group of medium to high atomic number together form a detector system of type B. Detectors of medium to high atomic number, besides the photoelectric effect, also exhibited a substantial Compton scattering behavior. The detector pairs formed by the detectors with $Z_{eff}>30$ are bidirectional. The detectors of lower atomic number $Z_{eff}\leq30$, on the other hand, are not suited for pair formation, because they do not have sufficiently high probabilities for the photoelectric effect Such a detector system is referred to as type A within the meaning of the invention.

Detector system of type A exist in two variants of embodiments, as type A separated and as type A mixed.

According to a further embodiment of the imaging detector system according to the invention of type A, the detectors of both groups with $Z_{eff}>30$ and $Z_{eff}\leq30$, respectively, belonging to the type A detector system are separated from each other spatially. If the radiation sources are located outside of the detector system, the detectors of the group with lower atomic number $Z_{eff}\leq30$ form the outer shell, they enclose the detectors of the other group from materials of medium to high atomic number $Z_{eff}>30$, which are concentrated in the interior. If the radiation sources are located within the detector system, the detectors of the group with lower atomic number $Z_{eff}\leq30$ are concentrated within the internal area, this is surrounded by an outer shell of the detectors of the other group from materials of medium to high atomic number $Z_{eff}>30$. Such a detector system is referred to type as A separated within the meaning of the invention.

According to a further embodiment of the imaging detector system according to the invention of type A, the detectors of both groups with $Z_{eff}>30$ and $Z_{eff}\leq30$, respectively, belonging to the type A detector system are mixed with each other spatially. All detectors are arranged in a one layer heterogeneous plane, wherein the plane may be plane or curved. Such a detector system is referred to as type A mixed within the meaning of the invention.

The imaging detector systems according to the invention of type A separated are closely related to the functional principle of the classical 2-plane Compton camera, however, they do have an important unique characteristic. In detector systems of type A separated, the group of the detectors of medium to high atomic number is interconnected to a detector system of type B. This new use form has effects on the original 2-plane Compton camera, which has represented the prior art for many decades. The rear detector plane in a 2-plane Compton camera is a detector system of type B. The number of usable detector pairs in type A and B detector systems of respectively n detectors is specified in tab. 1. For comparison purposes, also the numbers for a classical 2-plane Compton camera are listed. The type A detector system comprises 50% more pairs than the 2-plane Compton camera for the same number n of detectors, the type B detector system even twice as much pairs.

TABLE 1

|  | Number of detector pairs | | Gain in % |
|---|---|---|---|
|  |  | for n → ∞ | for n → ∞ |
| Classical 2-plane Compton camera (prior art) | $\frac{n^2}{4}$ | $\frac{n^2}{4}$ |  |
| Type A detector system | $\frac{n^2}{4}+\frac{n}{4}\left(\frac{n}{2}-1\right)$ | $\frac{3n^2}{8}$ | 50% |
| Type B detector system | $\frac{n}{2}(n-1)$ | $\frac{n^2}{2}$ | 100% |

Table 1: number of detector pairs for a detector system of n detectors with a configuration as a) classical 2-plane Compton camera, b) type A detector system and c) type B detector system. For the 2-plane Compton camera and for the type A detector system, it has been assumed that 50% of the detectors are of medium to high $Z_{eff}$, the other 50% of lower $Z_{eff}$.

According to a further embodiment of the imaging detector system according to the invention, a part of the system or the entire system is formed as a classical 2-plane Compton camera, which now is configured as imaging detector system of type A separated according to the invention by interconnecting the detectors. For this, the corresponding extensions have to be provided in the system electronics such that the rear camera plane of the 2-level Compton camera is configured as detector system of type B according to the invention. The rear camera plane, which according to the invention is formed as a detector system of type B, is integrated into the data analysis that already is available. The analysis unit processes the data of all detector pairs, which belong to the detector system according to the invention, including the data of the bidirectional detector pairs in the rear type B camera level.

Detector systems of type A mixed and of type B represent a further development of the Single Plane Compton camera, which has been described in US2012/0043467 for the first time. At this point, it will be explained how the imaging detector system according to the invention improves the prior art compared to US2012/0043467. The invention makes several improvements to the data acquisition system and to the analysis unit of the detector system.

The data acquisition systems described in US2012/0043467 sort the energy values $E_1$ and $E_2$ registered in the coincidence events—similar as with respect to a gamma spectrometer—into two histograms. By means of these histograms, energy mean values will be calculated later on. By means of such a data acquisition system, however, it is difficult, to recognize several radiation sources of a nuclide separately. The information required for the deconvolution of the data for several sources are not sufficiently stored by such a data acquisition system. The energy values $E_1$ and $E_2$ in a coincidence event are strongly correlated with each other due to the energy conservation. The information comprised in the correlation, however, is lost, if the energy values are stored in separate one-dimensional histograms.

An essential feature of the measurement value acquisition of the imaging detector system according to some embodiments of the invention is that a function $\sigma(E_1, E_2)$ is used, which is a function dependent on $E_1$ and $E_2$. Only a function dependent on both values $E_1$ and $E_2$ as, e. g., the asymmetry in eq. (4) is able to represent the direction information of the coincidence events appropriately. If, however, $E_1$ and $E_2$—as in US2012/0043467—are stored in separate histograms, a substantial part of the direction information is lost forever.

In addition to the quantitative improvement with respect to the measurement value $\sigma(E_1, E_2)$ and its direction-dependent information value, there will be a quantitative information extension with respect to the number of detector pairs, the measurement values of which are stored during a measurement, and are made accessible for the image reconstruction method. The methods described in US2012/0043467 only take coincidences along two selected directions into consideration, all others are dismissed. The determination of two directions, however, is the minimal selection that is necessary in order to calculate the azimuth and elevation angle of a radiation source. The substantial information loss by arbitrary limitation to detector pairs along two directions selected by the user is overcome by the invention. The imaging detector system according to the invention takes all pair combinations of radiation detectors into consideration, in which at least one detector has an atomic number of $Z_{eff}>30$. Without restriction to the direction of the detector pairs, all detector pairs, which are present in the imaging detector system according to the invention are used in the image reconstruction.

Further, the imaging detector system can include an analysis unit with an image reconstruction method, by means of which an image of a direction and an activity distribution, respectively, is calculated. Thereby, the functional range of the Single Plane Compton camera is extended, which up to now has been restricted to the direction measurement of a radiation source per nuclide.

The imaging detector system according to the invention may be adapted flexibly to very different operating conditions. Amongst others, the detector system according to the invention supports the use of different material combinations for different detector designs, which cover a wide spectrum of reconstruction tasks.

Detector systems of type A mixed and of type B have several characteristic features, which are not present in the classical 2-plane Compton camera. It should be emphasized that detector systems of type A mixed and of type B may be realized as one-layer surface area layouts for radiation detectors, either if these are plane or curved areas in space.

With respect to the detector systems of type B, the detectors in the one layer surface area layouts may consist of a uniform material. There no longer is a necessity to select two different materials. The former requirement, which is known from 2-plane Compton cameras that one material has to have a high, the other one a low atomic number, no longer exists for type B detector systems. In cases, where only few materials meet the constructive requirements for the radiation detectors, this property of type B detector systems may be very useful. One example are detector systems, which use the Temporal Imaging functional principle from U.S. Pat. No. 9,638,811 B2. Temporal Imaging systems of type B only require a detector material of medium to high atomic number, which meets the requirements of the pulse rise time below one nanosecond.

The detector topologies of the detector systems of type A and type B according to the invention are very flexible with respect to design, and may be one-, two-, or three-dimensional. The dimensionality of the detector assembly determines the field of vision.

The simplest imaging detector system according to the invention is achieved, if several radiation detectors are set up in a row. At a minimum, two radiation detectors are sufficient. The one-dimensional detector system has the field of vision of a semicircle.

According to an embodiment of the imaging detector system according to the invention, the latter comprises at least two radiation detectors, which are arranged in a one-dimensional detector row. Further, such a system has a field of vision from −90° to +90° perpendicular to the detector row. Such a detector system is referred to as 1-dimensional within the meaning of the invention.

Embodiments of the detector system with a two-dimensional arrangement of radiation detectors can be suitable for images in two perspectives. Hereby, it is distinguished between a hemispherical detector system and a 360° panoramic system within the meaning of the invention. The hemispherical detector system serves for imaging of radiation sources in a $2\pi$ half space in front of the detector plane. The 360° panoramic system is adapted for the two-dimensional detection of radiation sources in the detector plane.

According to an embodiment of the imaging detector system according to the invention, the latter comprises at least three radiation detectors, which are formed in a substantially two-dimensional arrangement with respect to each other. Further, such a system has a field of vision of a $2\pi$ spatial angle for radiation sources in a half space in front of the two-dimensional detector plane. Such a detector system is referred to as semi spherical within the meaning of the invention.

During the use of the hemispherical detector system, it should be taken care of all radiation sources being on the same side of the detector plane. The hemispherical detector system detects radiation sources in the entire $4\pi$ spatial angle, without the user being able to determine, whether a certain source is located in front of or behind the detector plane. It is implicitly assumed that the user knows on which side of the detector plane radiation sources are expected. The detector system has to be set up such that all radiation sources—seen from the point of view of the viewing person—are lying the same hemisphere in front of the detector plane.

According to an embodiment of the imaging detector system according to the invention, the latter comprises at least three radiation detectors, which are formed in a basically two-dimensional arrangement with respect to each other. Further, such a system comprises a 360° field of vision for radiation sources in the two-dimensional detector plane. Such a detector system is referred to as 360° panoramic system within the meaning of the invention.

The 360° panoramic system represents a new use form for the Single Plane Compton camera. The methods described in prior art for Single Plane Compton cameras are designed for the source detection within the field of vision of a hemisphere; however, they are not applicable, if the radiation sources are lying within the detector plane. The methods according to the prior art calculate the incidence direction of the gamma radiation as a sectional line of two so-called direction finding planes. In a borderline case, if the source lies within the detector plane, however, the direction finding planes are identical to the detector plane; a sectional line does not exist and the direction of the radiation source cannot be determined. The 360° panoramic system solves this problem and allows a two-dimensional direction measurement for radiation sources within the detector plane.

According to a further embodiment of the imaging detector system according to the invention, a part of the system or the entire system is designed as Single Plane Compton camera, which is extended to an imaging detector system according to the invention of type A mixed and/or is extended to an imaging detector system according to the invention of type B. For this, the data acquisition of the Single Plane Compton camera, which according to US2012/0043467 only stores energy spectra of coincidence events, is switched into list mode. The analysis unit is adapted such that for each coincidence event, a function $\sigma(E_1, E_2)$ dependent on both energy values $E_1$ and $E_2$ is calculated. Thus, the quantity of detector pairs is extended such that all pair combinations of detectors, which according to the invention belong to the detector system, are used for the image reconstruction. In particular, pair combinations in all available directions should be considered. The system electronics is to be adapted such that the data of all selected detector pairs is acquired. Further, the analysis unit creates the projection data $p(\underline{y})$ from the list mode data of the Single Plane Compton camera that is required for the image reconstruction according to the procedure of this invention. After the adjustment, the Single Plane Compton camera is available in one of two embodiments: as imaging detector system according to the invention of type A mixed and/or as imaging detector system according to the invention of type B. The Single Plane Compton camera that has been upgraded to an imaging detector system according to the invention may be used as hemispherical and/or as 360° panoramic system.

According to an embodiment of the imaging detector system according to the invention, the latter comprises at least four radiation detectors, which basically are formed in a three-dimensional arrangement with respect to each other. Further, the system comprises a sufficient number of detector pairs, the axes of which are well distributed over the $4\pi$ spatial angle. Such a system has a field of vision of a $4\pi$ spatial angle and is referred to as fully spherical within the meaning of the invention.

Embodiments for three-dimensional imaging detector systems according to the invention are specifically advantageous for applications in medical equipment manufacturing. Embodiments of three-dimensional detector systems of type B from modules of structurally identical detectors in one layer surface area layouts offer various construction advantages. For example, a SPECT scanner for highly energetic radionuclides, as for example I-131, may be realized as a detector system of type B. For SPECT scanners according to prior art, which use the Anger gamma camera principle, up to now, the highly energetic energy range is hardly accessible. In particular, combined SPECT and PET scanners may be designed according to the imaging detector systems of type B according to the invention. The full ring PET systems, which in the clinical environment are widely used, have many similarities with respect to design of the imaging detector systems of type B according to the invention which is proposed here. For a combined use as SPECT and PET scanners, possibly, new scintillation materials should be taken into consideration, the atomic number of which lies in a medium range, and which promote Compton scattering more than current PET scintillation crystals. A PET/SPECT hybrid scanner according to an embodiment of the imaging detector system according to the invention is particularly suitable for radio nuclides, as e.g., 1-124, which at the same time are positron and single photon emitters. For such radio nuclides, the PET/SPECT hybridization is specifically reasonable, because both radiation types may be combined in the image reconstruction. Also, the PET scanners may benefit by the consideration of Compton scattering events, which up to now only seldomly have been used in the image reconstruction.

Detector systems of type A mixed are similar to the ones of type B insofar as these also form one-layer surface area layouts. The heterogeneous detector faces of type A mixed systems offer advantages in the lower energetic range below 300 keV, as the probability for Compton scattering decreases in many materials. Then, it is advantageous to integrate detectors of lower atomic number into type A mixed systems, in order to ensure a good detector efficiency. Detector systems of type A mixed represent a suitable design for a SPECT scanner for radiopharmaceuticals on the basis of Tc-99m.

According to a further embodiment of the imaging detector system according to the invention, a part of the system or the entire system is designed as PET scanner, which is extended to an imaging detector system of type B according to the invention, and/or is extended to a PET/SPECT hybrid scanner. For this, a part of or all of the scintillation detectors which are present in the PET scanner including electronics, the system electronics and the analysis unit are used as imaging detector system according to the invention. For a use as imaging detector system according to the invention, the PET scanner is to be employed in connection with a radiopharmaceutical, which emits single photon gamma radiation. In an embodiment of the invention, the radiopharmaceutical emits single photon gamma radiation as well as positrons.

For the extension of the PET scanner to an imaging detector system according to the invention, a new system matrix $\underline{H}$ has to be created, which describes the PET scanner as Single Photon Compton Scanner of type B. The analysis unit stores the data in the list mode format, as it is common for PET scanners. The data acquisition has to be adapted to the energy range of the Single Photon gamma radiation. Coincidence events should be registered, the energy sum of which $E_1+E_2$ is adjusted to the characteristic radio nuclide energy of the radiopharmaceutical. According to the procedure of this invention, the projection data $\underline{p(y)}$ is to be created from the list mode data. The analysis unit processes the projection data $\underline{p(y)}$ using the system matrix $\underline{H}$. Optionally, also parts of the image reconstruction software belonging to the PET scanner may be used by the imaging detector system according to the invention, if these are suitable for such a use. After the extension, the PET scanner is available in one of two embodiments: as imaging detector system of type B according to the invention and/or as PET/SPECT hybrid scanner according to the invention. Both embodiments are imaging detector systems according to the invention for the near field. The embodiment of the PET/SPECT hybrid scanner may be used for imaging with radio nuclides, which (a) emit positrons, (b) emit single photon gamma radiation, and (c) emit positrons and single photon gamma radiation simultaneously. According to the embodiment (a), the PET/SPECT hybrid scanner is operated with the PET image reconstruction software, in the embodiment (b) with the image reconstruction software according to the invention, and in the embodiment (c) both image reconstruction methods for a PET/SPECT hybrid method are combined. The image reconstruction method in the embodiment (c) uses the image reconstruction software of the PET scanner as well as the image reconstruction software belonging to the imaging detector system according to the invention, which are fused with each other.

Subsequently, the imaging detector system according to the invention will be described in further detail by means of embodiments and in the drawings. The explanations are only exemplary and do not delimit the general concept of the invention. Also, embodiments may be combined arbitrarily. Examples for the method according to the invention are also described in the embodiments.

According to a preferred embodiment of the imaging detector system according to the invention, the latter detects radiation fields, which comprise a discrete and/or a continuous distribution of radiation, wherein the detector system is located in a geometric near and/or far field of the radiation field.

According to a further preferred embodiment of the imaging detector system according to the invention, the latter detects radiation sources, which emit the gamma, electron, positron, proton, ion, and/or neutron radiation.

According to a further preferred embodiment of the imaging detector system according to the invention, the radiation originates from the radioactive decay of one or more radio nuclides, and/or the radiation is the prompt gamma radiation, which is generated by the absorption of proton or ion radiation and target materials.

According to a further preferred embodiment of the imaging detector system according to the invention, the radiation has a low intensity, as this is, for example, the case in astronomy.

According to a further preferred embodiment of the imaging detector system according to the invention, the detectors comprise a scintillator with a photo detector, and/or a semiconductor material. The scintillator may comprise a pure or a doped material from the group of PVT, anthracene, stilbene, p-terphenyl, $CaF_2$, $BaF_2$, NaI, $CeBr_3$, $LaBr_3$, $LaCl_3$, $La(Br_xCl_{1-x})_3$, CsI, $SrI_2$, CLYC, CLBC, CLCB, CLLB, BGO, LSO, LYSO, GAGG, YAP and/or YAG. Further, the scintillator may be available as monolithic block or as pixelated scintillator module. Moreover, the photodetector may be a photomultiplier (PMT), a photomultiplier with spatial resolution (PSPMT), a silicon photomultiplier (SiPM), a silicon photomultiplier with spatial resolution (PS-SiPM), and/or a silicon photodiode. According to the invention, the semiconductor material may comprise a material from the group of Si, Ge, GaAs, CdTe and/or CdZnTe, and/or may have a planar or coaxial geometry. Also, the semiconductor material may be available with segmented or non-segmented contacts.

According to a further preferred embodiment of the imaging detector system according to the invention, the detector materials are subdivided virtually or physically into an arbitrary integer number of ≥1 voxels.

According to a further preferred embodiment of the imaging detector system according to the invention, the system electronics uses analog and/or digital electronics components.

According to a further preferred embodiment of the imaging detector system according to the invention, the analog electronic components comprise a combination of different modules, which comprise a high-voltage supply, a preamplifier, an amplifier, a pulse shaper, a charge integrator, a pulse height analyzer, a multichannel analyzer (MCA), and/or a coincidence circuit.

According to a further preferred embodiment of the imaging detector system according to the invention, the digital electronic components comprise a combination of various hardware and software components, which comprise a high-voltage supply, and A/D converter per detector voxel, a Field Programmable Gate Array (FPGA), a storage medium, a digital signal processor, and/or an analysis software.

According to a further preferred embodiment of the imaging detector system according to the invention, the interaction points ($\underline{d}_1$, $\underline{d}_2$) are determined by means of the properties of the detectors having spatial resolution, and/or by means of the present segmentation of the detectors.

According to a further preferred embodiment of the imaging detector system according to the invention, the interaction points ($\underline{d}_1$, $\underline{d}_2$) are defined as the spatial centers of a first and a second detector voxel of the detector voxels involved in a coincidence event.

According to a further preferred embodiment of the imaging detector system according to the invention, the functional value $\sigma(E_1, E_2)$ is defined according to $$\sigma(E_1, E_2) = (E_2 - E_1)/(E_1 + E_2)$$

According to a further preferred embodiment of the imaging detector system according to the invention, the analysis unit uses projection data $\underline{p}(\underline{y})$ for the reconstruction of the radiation field, which is defined as a function of the attributes $\underline{y} = \{\underline{d}_1, E_1, \underline{d}_2, E_2\}$.

According to a further preferred embodiment of the imaging detector system according to the invention, for each element of $\underline{p}$, a number of coincidence events is determined, which occur for a respective combination of a particular first detector voxel with a particular second detector voxel at a particular functional value $\sigma(E_1, E_2)$.

According to a further preferred embodiment of the imaging detector system according to the invention, for each element of $\underline{p}$, a number of coincidence events is determined, which occur for a respective combination of a particular first detection location $\underline{d}_1$ with a particular second detection location $\underline{d}_2$ at a particular functional value $\sigma(E_1, E_2)$.

According to a further preferred embodiment of the imaging detector system according to the invention, a selection condition for coincidence events is applied with respect to the energy sum $E_1 + E_2$ of the energies detected in both detector voxels of a pair.

According to a further preferred embodiment of the imaging detector system according to the invention, separate projection data $\underline{p}(\underline{y})$ is created for each detected radio nuclide, and/or the analysis unit calculates a separate image $\underline{f}(\underline{x})$ for each radio nuclide.

According to a further preferred embodiment of the imaging detector system according to the invention, the images $\underline{f}(\underline{x})$ represent an activity density, a flux density, and/or a dose rate density, and/or the images $\underline{f}(\underline{x})$ are tomographic sectional images of an activity distribution of radio nuclides (for example, also radiopharmaceuticals).

According to a further preferred embodiment of the imaging detector system according to the invention, all detectors basically have the same design, or at least two of the detectors have a different design with respect to each other.

According to a further preferred embodiment of the imaging detector system according to the invention, the latter comprises at least four detector voxels in a substantially three-dimensional arrangement, and has a field of vision of a $4\pi$ spatial angle.

According to a further preferred embodiment of the imaging detector system according to the invention, the latter comprises at least three detector voxels in a substantially two-dimensional arrangement, and has a hemispherical field of vision of a $2\pi$ spatial angle.

According to a further preferred embodiment of the imaging detector system according to the invention, the latter comprises at least three detector voxels in a substantially two-dimensional arrangement, and has a 360° field of vision in the plane of the radiation detectors.

According to a further preferred embodiment of the imaging detector system according to the invention, the latter comprises at least three detector voxels in a one dimensional detector row, and has a 180° field of vision from −90° to +90° perpendicular with respect to the detector row.

According to a further preferred embodiment of the imaging detector system according to the invention, the latter comprises a first group of detectors/voxels having an atomic number of $Z_{eff} > 30$, which have high probabilities for photoelectric absorption in the energy range from 100 keV to 3 MeV. Further, the detector system may optionally comprise a second group of detectors/voxels having an atomic number of $Z_{eff} \leq 30$, which have high probabilities for Compton scattering in the energy range from 100 keV to 3 MeV.

According to a further preferred embodiment of the imaging detector system according to the invention, data is required for all detector pairs/voxel pairs, which may be formed in combination from the quantity of all detectors/voxels, wherein such detector pairs/voxel pairs are excluded, in which both detectors/voxels belong to the second group having an atomic number of $Z_{eff} \leq 30$.

According to a further preferred embodiment of the imaging detector system according to the invention, the mixed detector pairs/voxel pairs, which respectively comprise one detector/voxel from the first group and one detector/voxel from the second group, are unidirectional, wherein the radiation is predominantly scattered in one direction.

According to a further preferred embodiment of the imaging detector system according to the invention, the detector pairs/voxel pairs of the first group having an atomic number of $Z_{eff} > 30$, are bidirectional, wherein the radiation is scattered in both directions with a similar intensity.

According to a further preferred embodiment of the imaging detector system according to the invention, the entirety of detectors/voxels, which are comprised in the detector system, has a homogeneous or heterogeneous ring-shaped, tubular, cylindrical, spherical, polyhedral, and/or other geometrical shape.

According to a further preferred embodiment of the imaging detector system according to the invention, the entirety of the detectors/voxels, which are comprised in the detector system, in addition to the first shape, comprises a second homogeneous or heterogeneous ring-shaped, tubular, cylindrical, spherical, polyhedral, and/or other geometrical shape, wherein the second shape is inscribed in the first shape, or wherein the second shape is arranged in an interior region, which encloses the first shape as outer shell.

According to a further preferred embodiment of the imaging detector system according to the invention, the first and/or the second shapes are/is arranged in one or more central detectors.

According to a further preferred embodiment of the imaging detector system according to the invention, a part of the system or the entire system is configured as detection device for radiation sources, as a Compton camera, as a Compton telescope, as a detector system, for example, according to U.S. Pat. No. 9,638,811 B2, as a SPECT scanner, as a PET/SPECT hybrid scanner, as a SPECT sensor and/or as a PET/SPECT hybrid sensor.

According to a preferred embodiment of the method according to the invention, the latter, in addition comprises, partially or entirely, the following steps:
calibrating the signals of all detector voxels as absorbed radiation energy E;
determining a suitable coordinate system;
creating one or more projection data sets $\underline{p}(\underline{y})$, which acquire the numbers of coincidence events, which are counted for a respective combination of a particular first detector voxel $\underline{d}_1$ with a particular second detector voxel $\underline{d}_2$ at a particular functional value $\sigma(E_1, E_2)$, wherein a separate projection data set $\underline{p}(\underline{y})$ is created for each radio nuclide;
creating one or more system matrixes $\underline{H}$ for each radio nuclide to be detected;
creating and validating the system matrixes $\underline{H}$ by means of measurements with the detector system or by means of Monte Carlo simulations or by means of a theoretical model;
transferring all system matrixes $\underline{H}$ to an algorithm of the image reconstruction, which processes the projection data $\underline{p}(\underline{y})$ and calculates the images $\underline{f}(\underline{x})$.

Other details, objects, and advantages of the embodiments of the detection apparatus and detection method will become apparent as the following description of certain exemplary embodiments thereof proceeds.

BRIEF DESCRIPTION OF THE DRAWINGS

The invention and exemplary embodiments thereof will be described below in further detail in connection with the drawings. It should be understood that like reference characters used in the drawings may identify like components. In the drawings:

FIG. 5a is a schematic illustration that is not to scale for the selection and identification of a first detector pair P1 in the detector system of FIG. 5d according to an embodiment of the imaging detector system according to the invention;

FIG. 5b is a schematic illustration that is not to scale for the selection and identification of a second detector pair P2 in the detector system of FIG. 5d according to an embodiment of the imaging detector system according to the invention;

FIG. 5c is a schematic illustration that is not to scale for the selection and identification of a third detector pair P3 in the detector system of FIG. 5d according to an embodiment of the imaging detector system according to the invention;

FIG. 5d is a schematic illustration that is not to scale for the selection and identification of detector pairs using the example of a detector system of three detectors according to an embodiment of the imaging detector system according to the invention;

FIG. 7a is a schematic illustration that is not to scale for the selection and identification of detector pairs in a first direction P1 in the detector system of FIG. 7e according to an embodiment of the imaging detector system according to the invention;

FIG. 7b is a schematic illustration that is not to scale for the selection and identification of detector pairs of a second direction P2 in the detector system of FIG. 7e according to an embodiment of the imaging detector system according to the invention;

FIG. 7c is a schematic illustration that is not to scale for the selection and identification of detector pairs in a third direction P3 in the detector system of FIG. 7e according to an embodiment of the imaging detector system according to the invention;

FIG. 7d is a schematic illustration that is not to scale for the selection and identification of detector pairs in a fourth direction P4 in the detector system of FIG. 7e according to an embodiment of the imaging detector system according to the invention;

FIG. 7e is a schematic illustration that is not to scale for the selection and identification of detector pairs using the example of a detector system of four detectors according to an embodiment of the imaging detector system according to the invention;

FIG. 9a is a schematic illustration that is not to scale of a 2-plane Compton camera according to an embodiment of the prior art;

FIG. 9b is a schematic illustration that is not to scale of a 2-plane Compton camera, which is configured as an imaging detector system of type A separated according to an embodiment of the imaging detector system according to the invention;

FIG. 10a is a schematic illustration that is not to scale of a two-dimensional detector system with hemispherical field of vision according to an embodiment of the imaging detector system according to the invention;

FIG. 10b is a schematic illustration that is not to scale of a two-dimensional detector system with a 360° field of vision in the detector plane according to an embodiment of the imaging detector system according to the invention;

FIG. 12a is a schematic illustration that is not to scale of a two-dimensional detector system of type A according to an embodiment of the imaging detector system according to the invention;

FIG. 12b is a schematic illustration that is not to scale of a cube-shaped detector system of type A according to an embodiment of the imaging detector system according to the invention;

FIG. 12c is a schematic illustration that is not to scale of a tetrahedron-shaped detector system of type A according to an embodiment of the imaging detector system according to the invention;

FIG. 16a is a graph comparing the simulation results for cerbromide-plastic and cerbromide-cerbromide detector pairs for a scintillator thicknesses of 25 mm;

FIG. 16b is a graph comparing the simulation results for cerbromide-plastic and cerbromide-cerbromide detector pairs for a scintillator thicknesses of 50 mm;

FIG. 16c is a graph comparing the simulation results for cerbromide-plastic and cerbromide-cerbromide detector pairs for a scintillator thicknesses of 75 mm;

DETAILED DESCRIPTION

Figure 1:
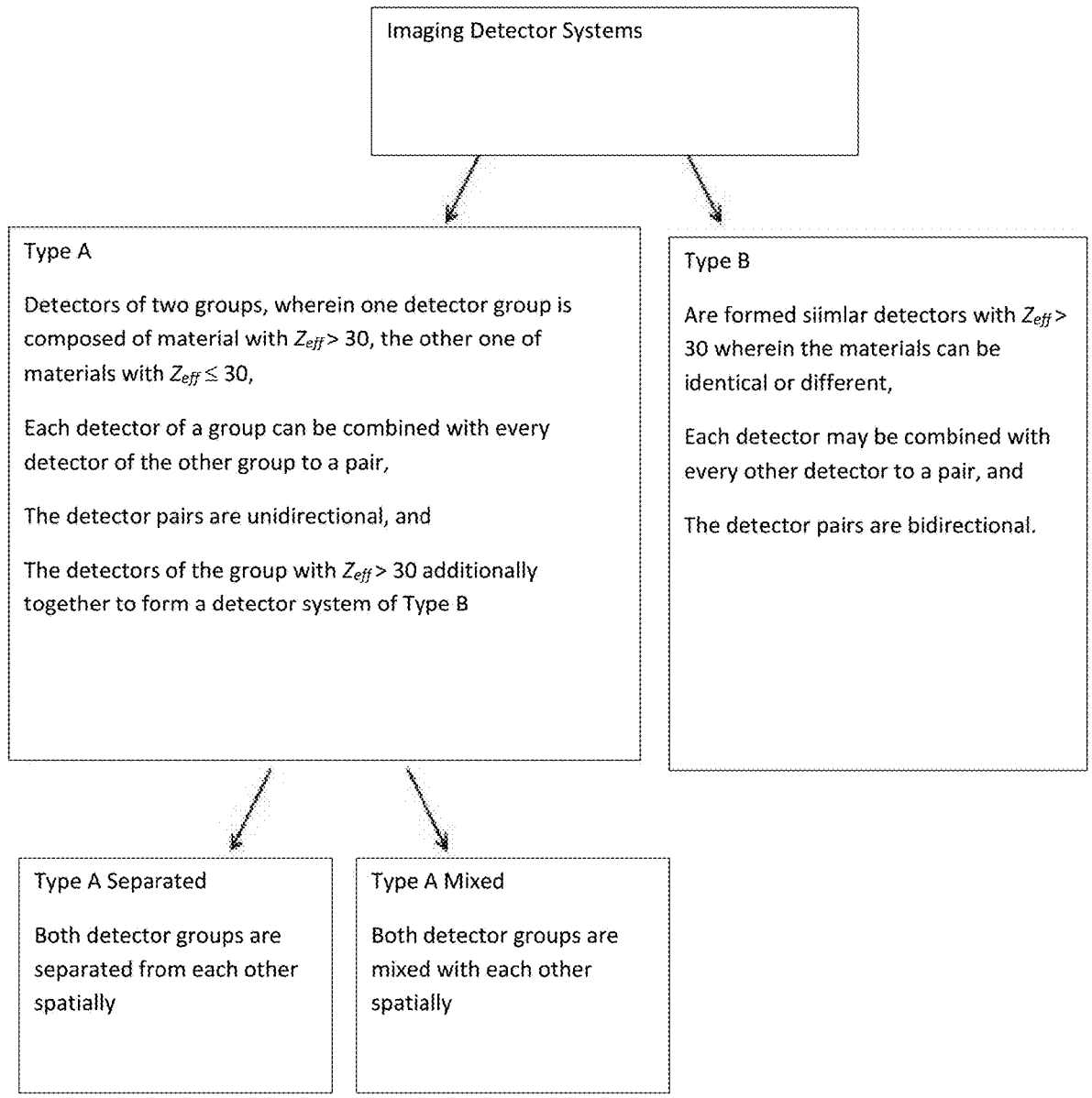
FIG. 1 shows an exemplary classification scheme for imaging detector systems into type A separated, type A mixed, and type B, according to three embodiments of the imaging detector system according to the invention.

FIG. 1 shows an exemplary classification scheme for detector systems of type A and type B. Type A detector systems may be further differentiated according to the spatial arrangement of the detectors into type A separated and type A mixed.

Figure 2A:
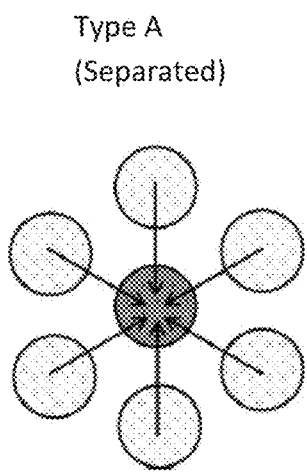
FIG. 2a is a schematic illustration that is not to scale of an exemplary annular detector system of type A separated according to an embodiment of the imaging detector system.
Figure 2B:
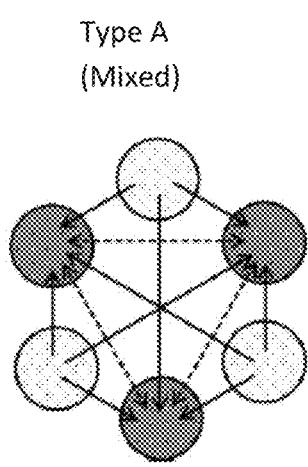
FIG. 2b is a schematic illustration that is not to scale of an exemplary annular detection system of type A mixed according to an embodiment of the imaging detector system.
Figure 2C:
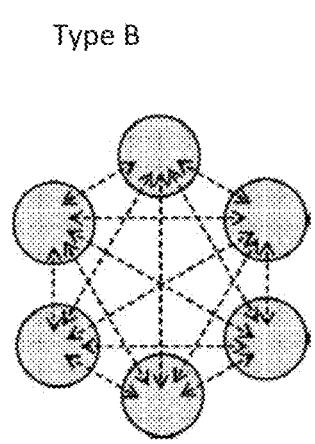
FIG. 2c s a schematic illustration that is not to scale of an exemplary annular detection system of type B according to an embodiment of the imaging detector system according to the invention.

FIGS. 2a-c illustrate exemplary classification schemes of FIG. 1 using the example of annular detector systems. With respect to the arrangement type A separated, the detectors of lower atomic number form an outer ring around an inner central detector of medium to high atomic number. In the arrangement type A mixed, there is no central detector, each detector in the ring is surrounded by two detectors of the respectively other group. The arrangement of type B is a ring of similar detectors, in which all detectors consist of a material of medium to high atomic number.

Figure 3:
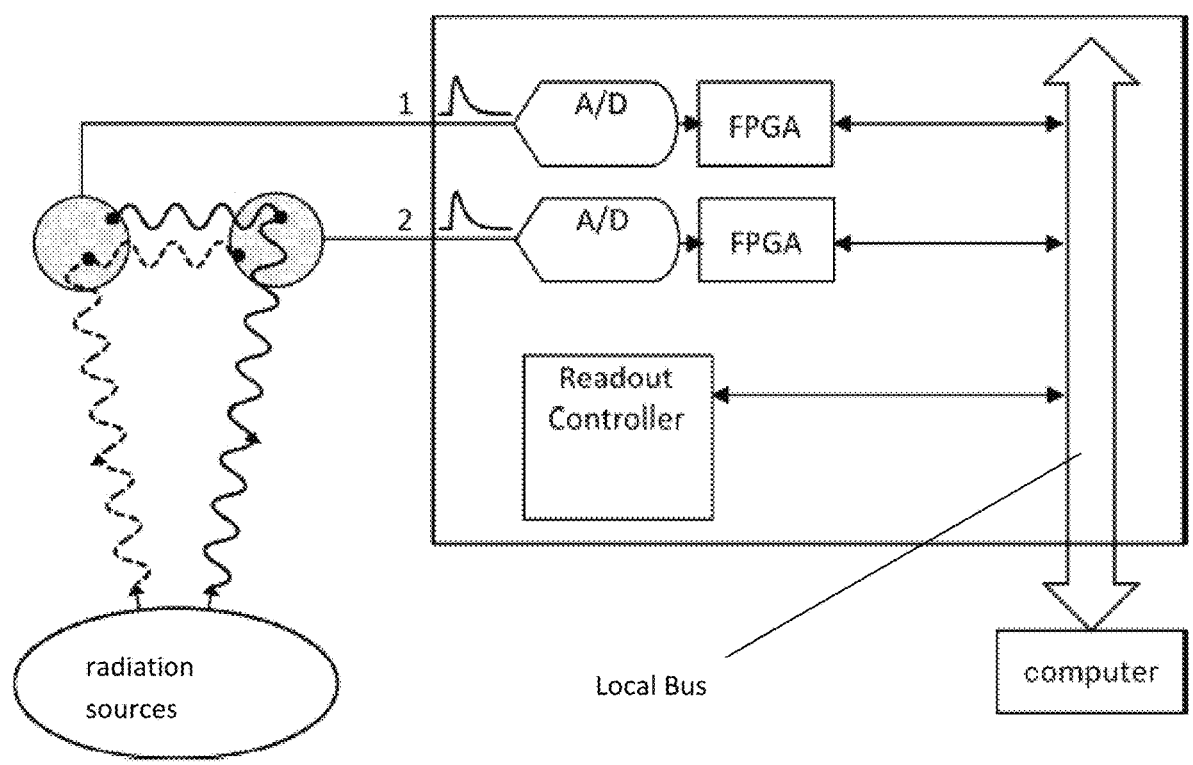
FIG. 3 is a schematic illustration that is not to scale of an exemplary detector system of two detectors with components of the system electronics according to an embodiment of the imaging detector system according to the invention.

FIG. 3 shows a block diagram with an embodiment of the system electronics for the detector system made up by two detectors. The detector pairs shown consists of two detectors of medium to high atomic number. The radiation flux between the detectors is bidirectional.

Figure 4A:
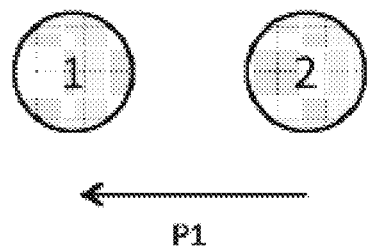
FIG. 4a is a schematic illustration that is not to scale of an exemplary detector system of two detectors according to the invention.
Figure 4B:
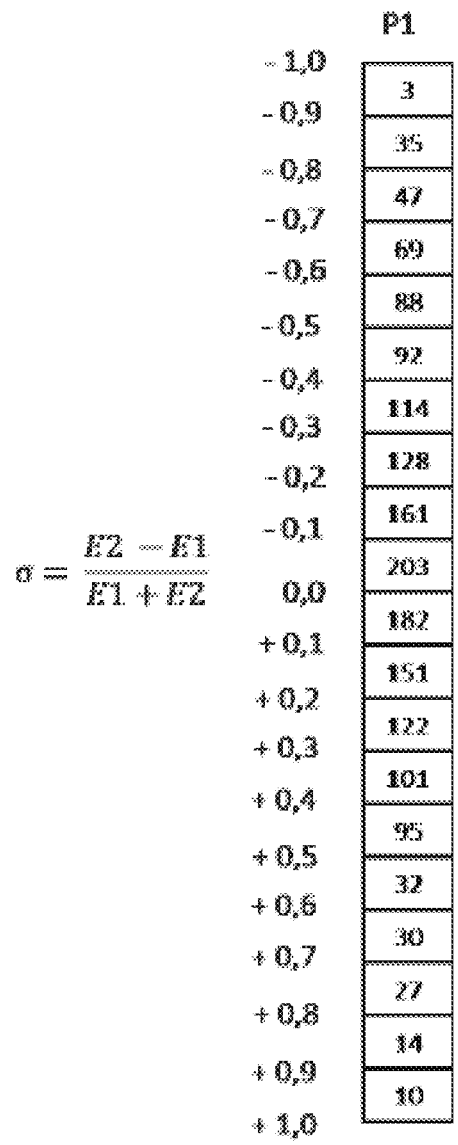
FIG. 4b is a schematic illustration that is not to scale of the data acquisition of an exemplary detector system of two detectors according to an embodiment of the imaging detector system according to the invention.

FIG. 4 schematically illustrates the exemplary data acquisition using the example of a detector system made up of two detectors of medium to high atomic number. FIG. 4a shows the detector system with the detector pair P1. FIG. 4b shows the data acquisition for the detector system of FIG. 4a. The number of coincidence events, which are registered at a particular value of a function $\sigma(E_1, E_2)$ that is dependent on both energy values $E_1$ and $E_2$ is determined for the detector pair P1. The table shown in FIG. 4b is a tabular illustration of the projection data p(y) according to the invention.

FIG. 5 schematically illustrates an exemplary embodiment of the selection and identification of detector pairs using the example of a detector system made up by three detectors of medium to high atomic number. The detector system illustrated in FIG. 5 comprises three bidirectional detector pairs P1, P2, and P3. FIG. 5a, 5b and 5c show examples for the identification of the detectors of a first pair P1 (FIG. 5a), a second pair P2 (FIG. 5b), and a third pair P3 (FIG. 5c) with the numbers 1 and 2, respectively.

Figures 6A, 6B:
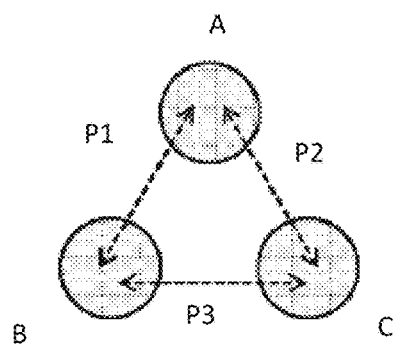
FIG. 6a is a schematic illustration it is not to scale of an exemplary detector system of three detectors according to the invention.
FIG. 6b is a schematic illustration that is not to scale of the data acquisition of an exemplary detector system of three detectors according to an embodiment of the imaging detector system according to the invention.

FIG. 6 schematically illustrates the exemplary process for data acquisition using the example of the detector system from FIG. 5. FIG. 6a shows the detector system with three detector pairs P1, P2, and P3. FIG. 6b shows the data acquisition for the detector system in FIG. 6a. For each detector pair P1, P2, and P3, the number of coincidence events is determined, which are registered at a particular value of a function $\sigma(E_1, E_2)$ that is dependent on both energy values $E_1$ and $E_2$. The table shown in FIG. 6b is a tabular illustration of the projection data p(y) according to this invention.

FIG. 7 schematically illustrates an exemplary selection and identification of detector pairs using the example of a detector system made up by four detectors of medium to high atomic number. The detector system illustrated in FIG. 7 comprises six bidirectional detector pairs. For embodiments of the invention in the far field, it is sufficient to select for directions P1, P2, P3 and P4. In the horizontal and in the vertical directions, there are two detector pairs respectively, which have the same direction. In the far field, both horizontal detector pairs may be detected together in the direction P1, as well as those vertical detector pairs may be detected together in the direction P2. FIGS. 7a, 7b, 7c and 7d show examples from the identification of the detectors of a first direction P1 (FIG. 7a), a second direction P2 (FIG. 7b), the third direction P3 (FIG. 7c), and a fourth direction P4 (FIG. 7d) having the numbers one and two, respectively.

Figures 8A, 8B:
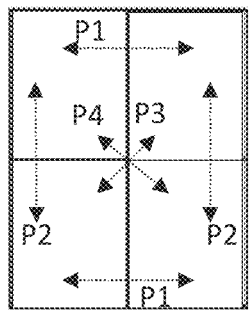
FIG. 8a is a schematic illustration that is not to scale of an exemplary detector system of four detectors according to the invention.
FIG. 8b is a schematic illustration that is not to scale of the data acquisition of an exemplary detector system of four detectors according to an embodiment of the imaging detector system according to the invention.

FIG. 8 schematically illustrates an exemplary embodiment of data acquisition using the example of the detector system of FIG. 7. FIG. 8a shows the detector system with four detector pairs P1, P2, P3, and P4. FIG. 8b shows the data acquisition for the detector system in FIG. 8a. For each of the four directions P1, P2, P3, and P4, the number of coincidence events is determined, which are registered at a particular value of a function $\sigma(E_1, E_2)$ that is dependent on both energy values $E_1$ and $E_2$. The table shown in FIG. 8b is a tabular illustration of the projection data $\underline{p}(\underline{y})$ according to this invention.

FIG. 9a schematically illustrates the extension of a 2-plane Compton camera to an imaging detector system of type A separated according to exemplary embodiments of the invention. The 2-plane Compton camera shown in FIG. 9a with eight detectors comprises 16 unidirectional detector pairs.

FIG. 9b schematically illustrates an exemplary embodiment in which four detectors of the rear detector plane may be combined into 6 bidirectional detector pairs, as illustrated in FIG. 9b. In a detector system of type A separated, the data of 16 unidirectional and 6 bidirectional detector pairs may be acquired and processed together. The image reconstruction methods of the 2-plane Compton camera may be extended correspondingly, in order to integrate the additional data sets of the rear type B detector plane into the image reconstruction. By the adjustment, the number of detector pairs increases from 16 to 22, whereby the efficiency and the image quality of the 2-plane Compton camera are increased.

FIGS. 10a-10b schematically shows two use variants for detector systems with a two-dimensional arrangement of the detectors. In FIG. 10a, the exemplary two-dimensional detector system is illustrated as a hemispherical detector system, in FIG. 10b, the system is illustrated as an exemplary 360° panoramic system. The panoramic system of FIG. 10b, serves for measurement of two-dimensional direction distributions in the detector plane. The change of perspective may be effected by adjusting the image reconstruction method.

Figure 11A:
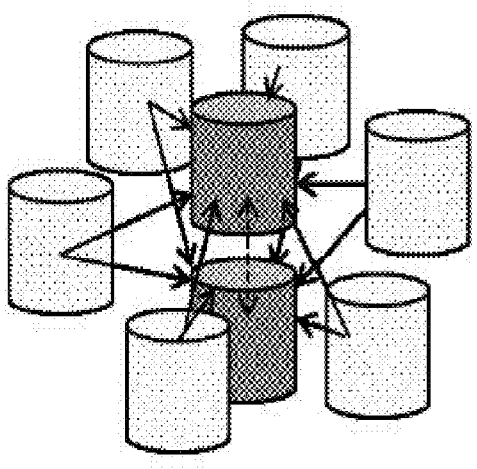
FIG. 11a is a schematic illustration that is not to scale of a fully spherical detector system of type A according to an embodiment of the imaging detector system according to the invention.
Figure 11B:
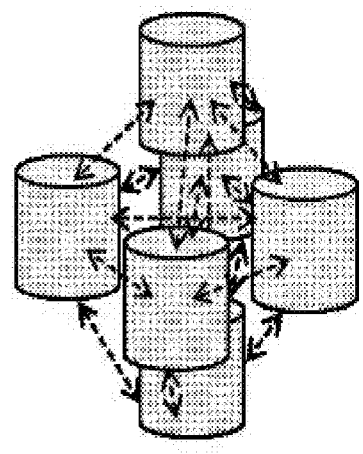
FIG. 11b is a schematic illustration that is not to scale of a fully spherical detector system of type B according to an embodiment of the imaging detector system according to the invention.

FIG. 11a-11b shows a schematic illustration of two fully spherical detector systems.

The fully spherical detector system of type A shown in FIG. 11a has the shape of a hexagon made up by six external detectors, which are grouped around two inner detectors. The detector system comprises twelve unidirectional detector pairs made up by respectively one inner and one outer detector. The two inner detectors additionally form a bidirectional detector pair. This thirteenth detector pair made up by the two inner detectors supplies additional information on the height angle of the radiation sources.

FIG. 11b shows a schematic illustration of a fully spherical detector system of type B. The sixth detectors, which are arranged as an octahedron, may be combined into 15 bidirectional detector pairs.

FIG. 12a-c shows a further detector variant of type A.

The two-dimensional detector system illustrated in FIG. 12a schematically illustrates an embodiment that consists of three inner detectors of higher atomic number and six out of detectors of lower atomic number. They form a triangle in a hexagon. This yields 18 unidirectional and 3 bidirectional detector pairs (21 detector pairs in total).

FIG. 12b schematically illustrates an embodiment that shows a cube shaped detector system. Four corners of the cube are occupied by detectors of high atomic number, these together form a tetrahedron. The tetrahedron made up by four detectors of high atomic number yields six bidirectional detector pairs. Additionally, incident radiation is also scattered from the four detectors of lower atomic number onto respectively four detectors of high atomic number, whereby 16 further unidirectional detector pairs are added. In total, 22 detector pairs are available.

FIG. 12c schematically illustrates an exemplary embodiment that consists of a small tetrahedron, which is surrounded by a larger tetrahedron. The inner tetrahedron comprises four detectors of high atomic number, the outer tetrahedron comprises four detectors of low atomic number. The four detectors of high atomic number respectively are located at the face centers of the four lateral surfaces of the outer tetrahedron. The smaller tetrahedron made up by the detectors of high atomic number has a third of the lateral length of the enclosing outer tetrahedron. The "tetrahedron in tetrahedron" has 16 unidirectional and 6 bidirectional detector pairs (22 detector pairs in total).

Figure 13A:
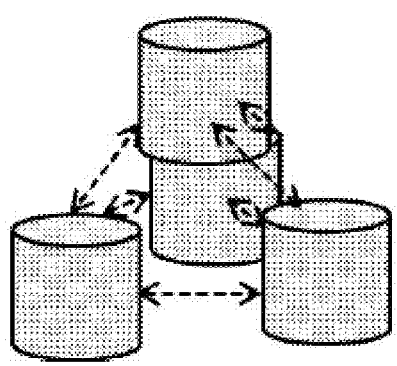
FIG. 13a is a schematic illustration that is not to scale of a tetrahedron-shaped detector system of type B according to an embodiment of the imaging detector system according to the invention.
Figure 13B:
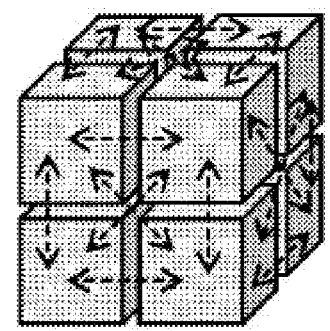
FIG. 13b is a schematic illustration that is not to scale of a cube-shaped detector system of type B according to an embodiment of the imaging detector system according to the invention.

FIGS. 13a-b shows further variants for detector systems of type B. In FIG. 13a, an arrangement of four detectors in form of a tetrahedron with six bidirectional detector pairs is illustrated. The detector cube in FIG. 13b consists of eight detectors with 28 bidirectional detector pairs.

Figure 14:
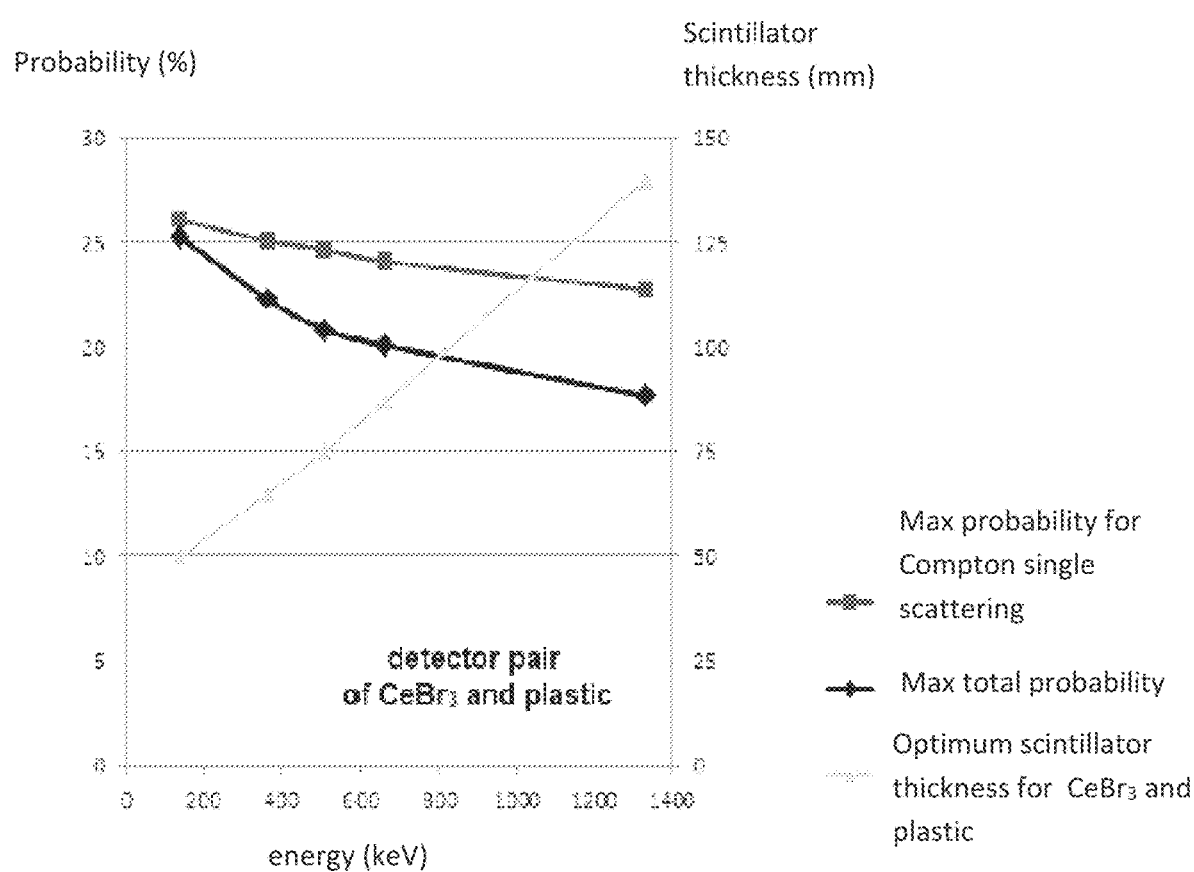
FIG. 14 is a diagram with simulation results for detector pairs of a cerbromide and a plastic detector according to an embodiment of the imaging detector system according to the invention.

FIG. 14 shows simulation results for unidirectional detector pairs with a cerbromide and a plastic detector. The diagram illustrates the influence of the scintillator thickness on the interaction probabilities for Compton single scattering $P_{CSS}$ in plastic scintillators and the photoelectric effect $P_{PE}$ in cerbromide crystals. The curves show the maximum probability $P_{CSS}^{max}=\mathrm{Max}(P_{CSS})$ and the maximum total probability $P_{ges}^{max}=\mathrm{Max}(P_{CSS} \cdot P_{PE})$ as a function of the gamma energy assuming that both scintillators have the same dimension. In the energy range from 140 keV to 1400 keV, $P_{CSS}^{max}$ always is above 20%, presumed that the scintillator thickness has been selected optimally. Moreover, it is illustrated at which scintillator thickness the maximum total probability $P_{ges}^{max}$ is reached.

Figure 15:
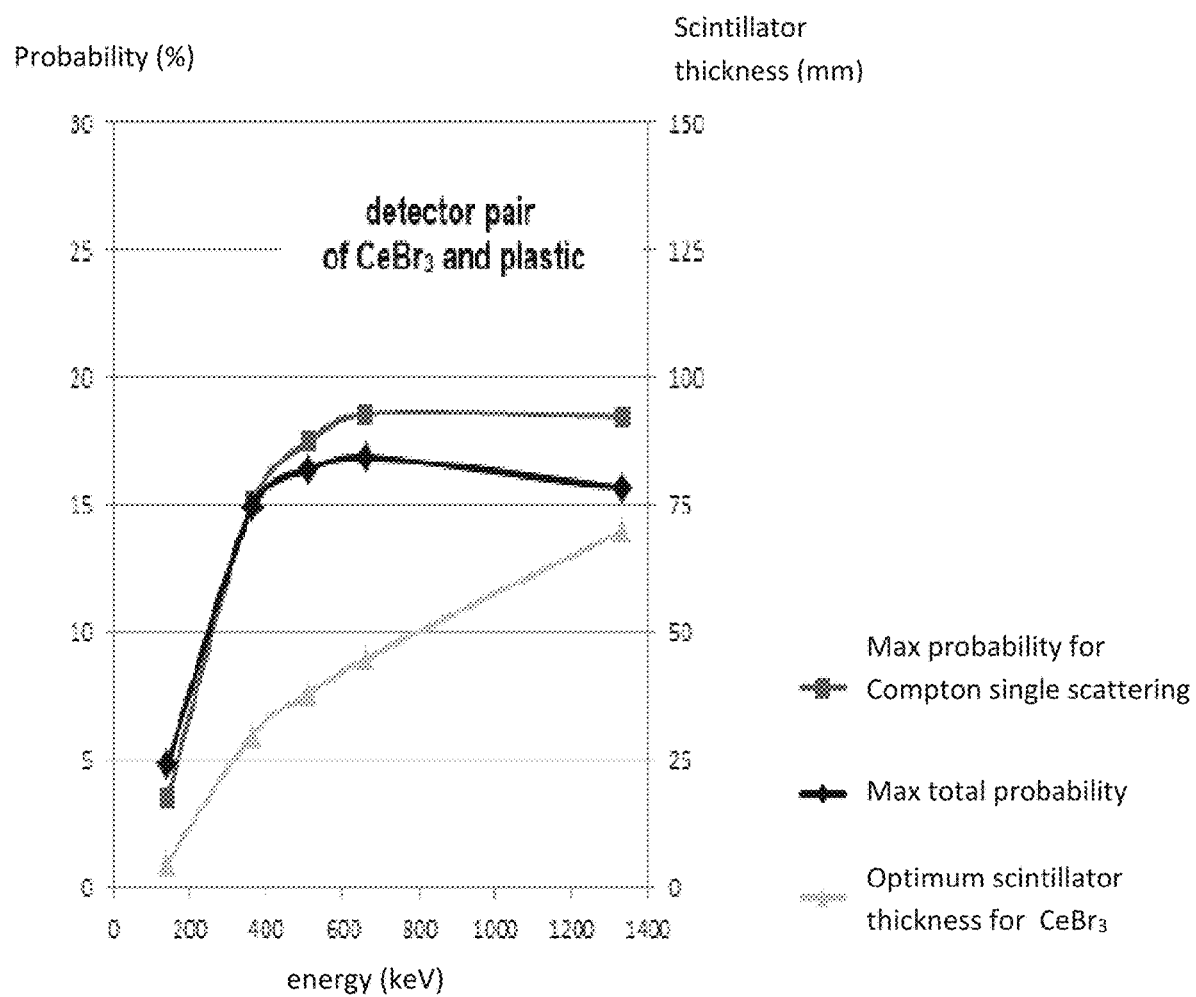
FIG. 15 is a diagram with simulation results for detector pairs of two cerbromide detectors according to an embodiment of the imaging detector system according to the invention.

FIG. 15 shows simulation results for bidirectional detector pairs of two cerbromide detectors. It is shown, which interaction probabilities for Compton single scattering $P_{CSS}^{max}=\mathrm{Max}(P_{CSS})$ and which total probabilities $P_{ges}^{max}=\mathrm{Max}(2 \cdot P_{CSS} \cdot P_{PE})$ may be achieved under optimum conditions. Below 300 keV, $P_{CSS}^{max}$ decreases rapidly. In the energy range from 662 to 1332 keV, on the other hand, $P_{CSS}^{max}$ is nearly constant at 18.5%. The curve for optimum scintillator thickness shows the thickness, at which—depending on the energy of the incident radiation—the maximum total probability $P_{ges}^{max}$ is reached.

Figure 16A:
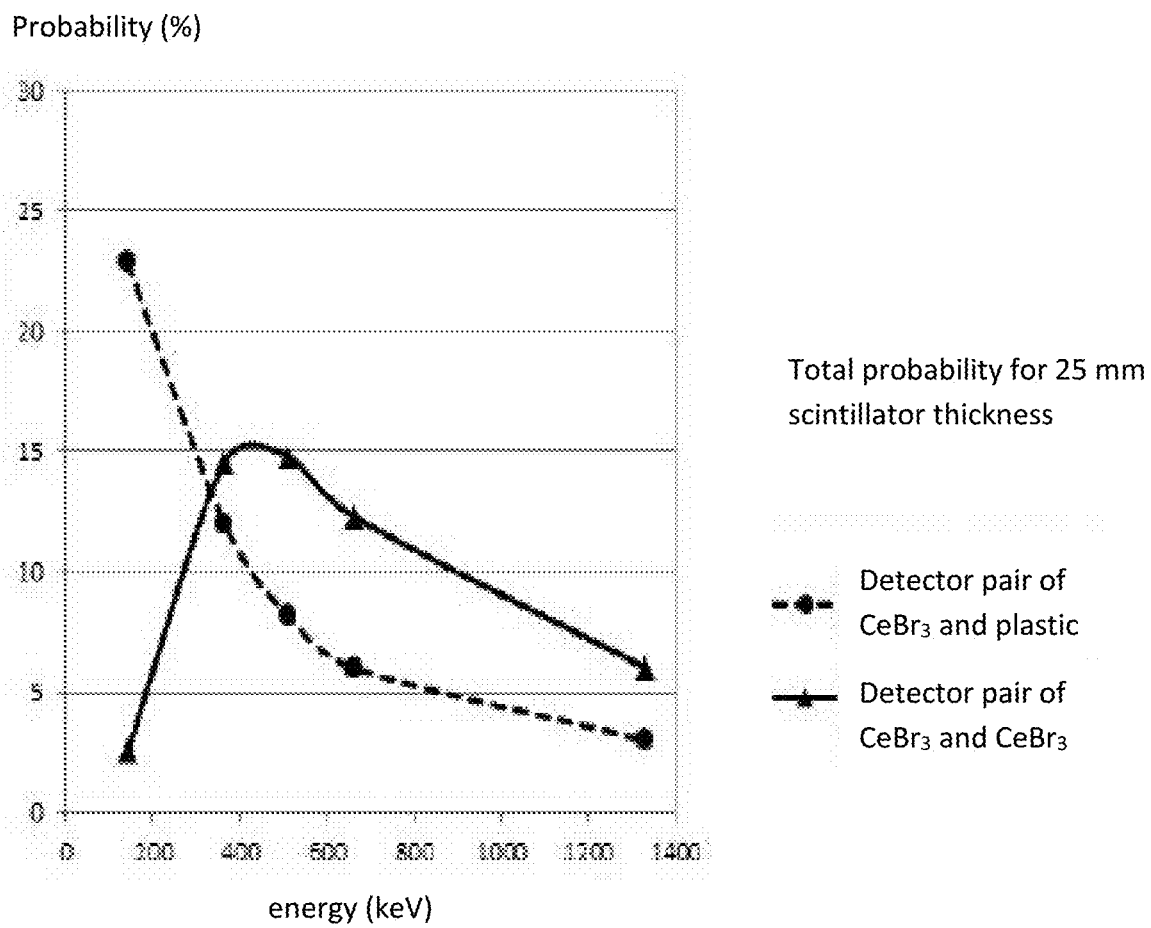
FIG. 16a-c are three diagrams with simulation results for cerbromide-plastic and cerbromide-cerbromide detector pairs according to an embodiment of the imaging detector system according to the invention.

FIG. 16a is a graph comparing the simulation results for cerbromide-plastic and cerbromide-cerbromide detector pairs for a scintillator thicknesses of 25 mm. For cerbromide-plastic detector pairs, the total probability is calculated by $P_{ges}=P_{CSS} \cdot P_{PE}$, for cerbromide-cerbromide detector pairs by $P_{ges}=2 \cdot P_{CSS} \cdot P_{PE}$.

Figure 16B:
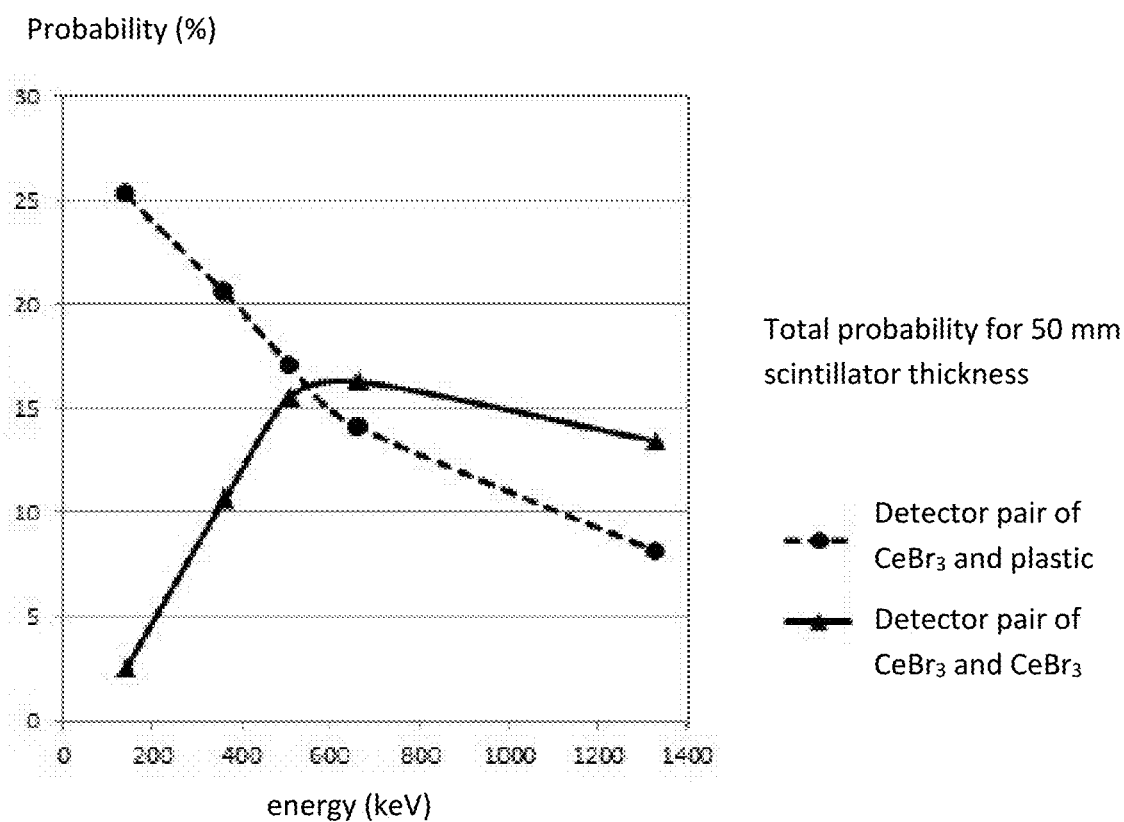

FIG. 16b is a graph comparing the simulation results for cerbromide-plastic and cerbromide-cerbromide detector pairs for a scintillator thicknesses of 50 mm. For cerbromide-plastic detector pairs, the total probability is calculated by $P_{ges}=P_{CSS} \cdot P_{PE}$, for cerbromide-cerbromide detector pairs by $P_{ges}=2 \cdot P_{CSS} \cdot P_{PE}$.

Figure 16C:
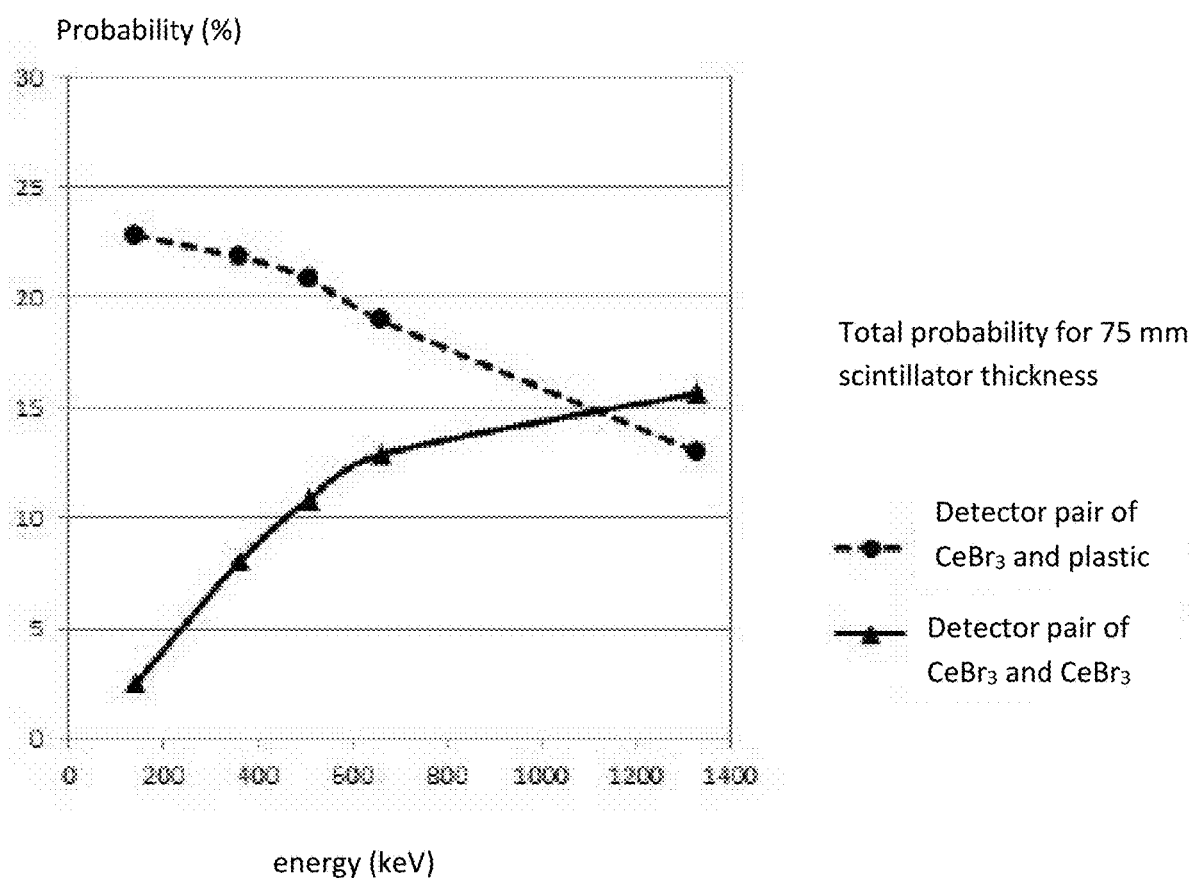

FIG. 16c is a graph comparing the simulation results for cerbromide-plastic and cerbromide-cerbromide detector pairs for a scintillator thicknesses of 75 mm. For cerbromide-plastic detector pairs, the total probability is calculated by $P_{ges}=P_{CSS} \cdot P_{PE}$, for cerbromide-cerbromide detector pairs by $P_{ges}=2 \cdot P_{CSS} \cdot P_{PE}$.

Figure 17:
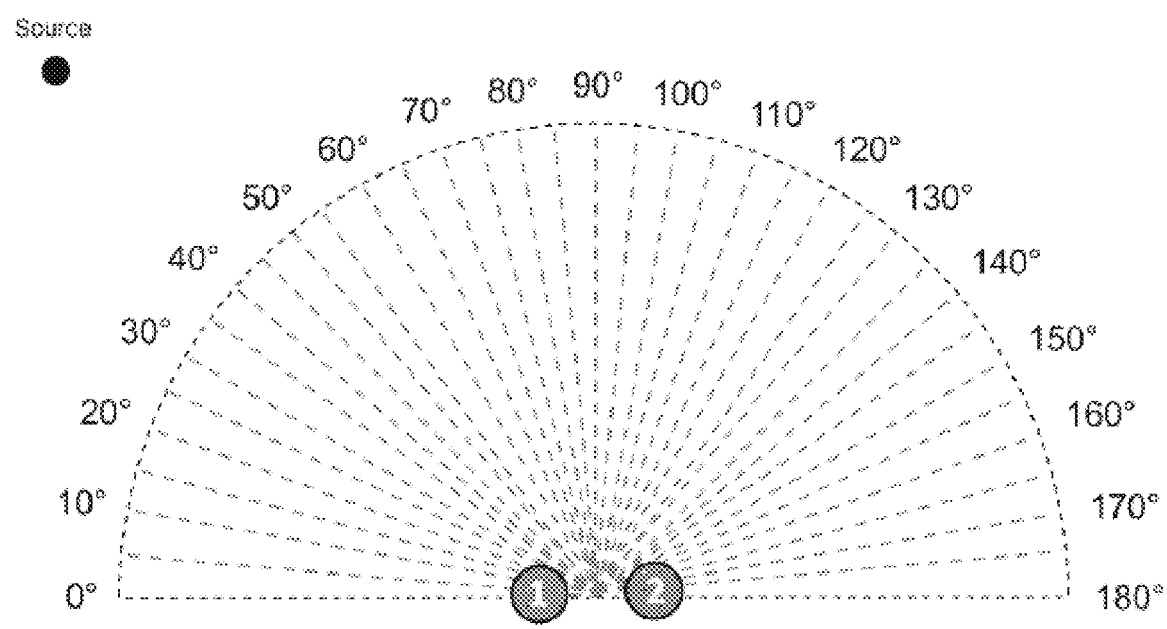
FIG. 17 is a schematic illustration that is not to scale of a measurement set up for the one-dimensional detector system from two radiation detectors according to an embodiment of the imaging detector system according to the invention.

FIG. 17 shows a schematic illustration for a measurement setup with a 1-dimensional detector system made up by two radiation detectors. The measurement setup may be realized as unidirectional or as bidirectional detector system. The field of vision of the detector system is limited to a semicircle.

Figure 18:
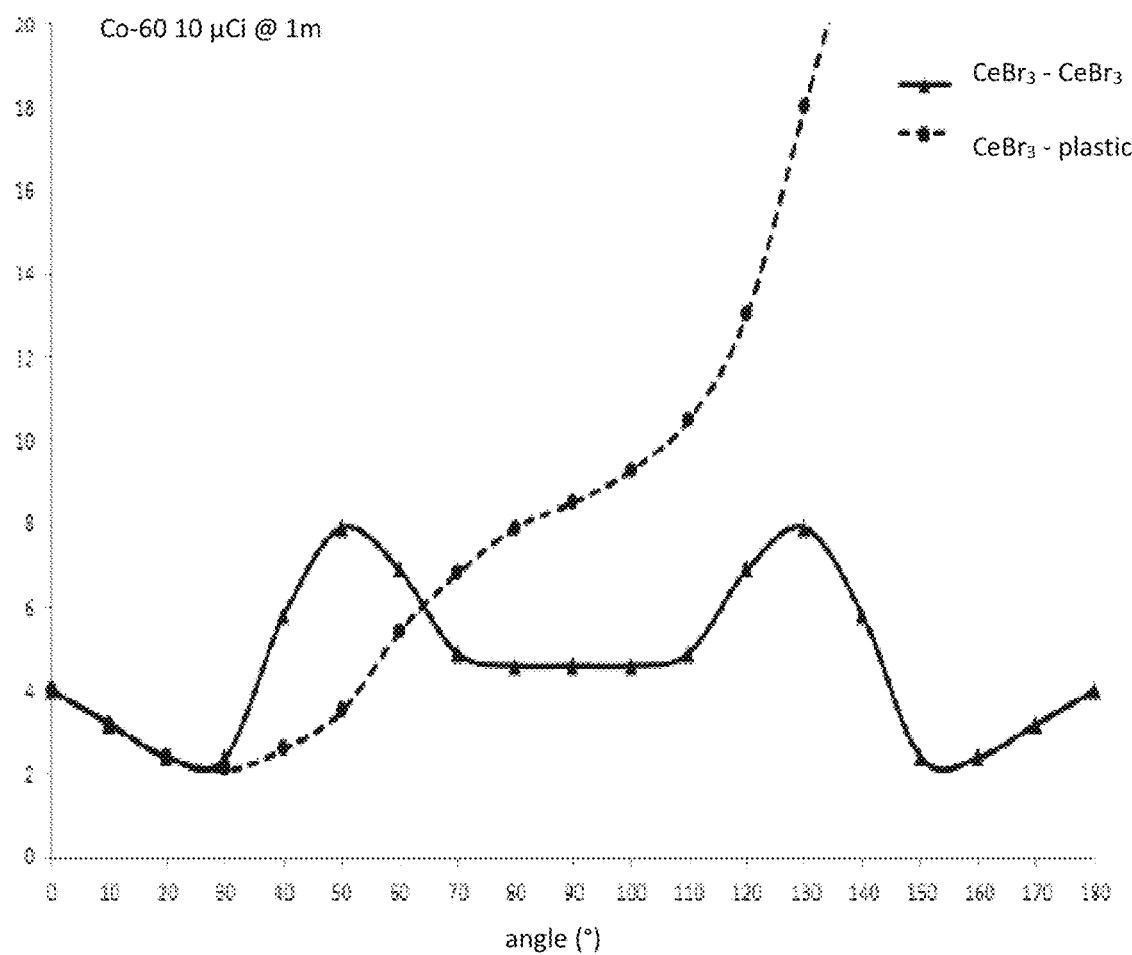
FIG. 18 is a diagram with measurement results for the two detector arrangement for direction measurement of a Co-60 source shown in FIG. 17 according to an embodiment of the imaging detector system according to the invention.

FIG. 18 shows measurement results for the two-detector-arrangement shown in FIG. 17 for direction measurement of a Co-60 source. The minimum measurement time for an accuracy of the angle of ±10° is illustrated as a function of the angle of incidence, measured in two detector variants with a cerbromide-cerbromide and a cerbromide-plastic detector pair. The local dose rate of the Co-60 source (10 μCi) was 0.11 μSv/h at the measurement point.

Figure 19:
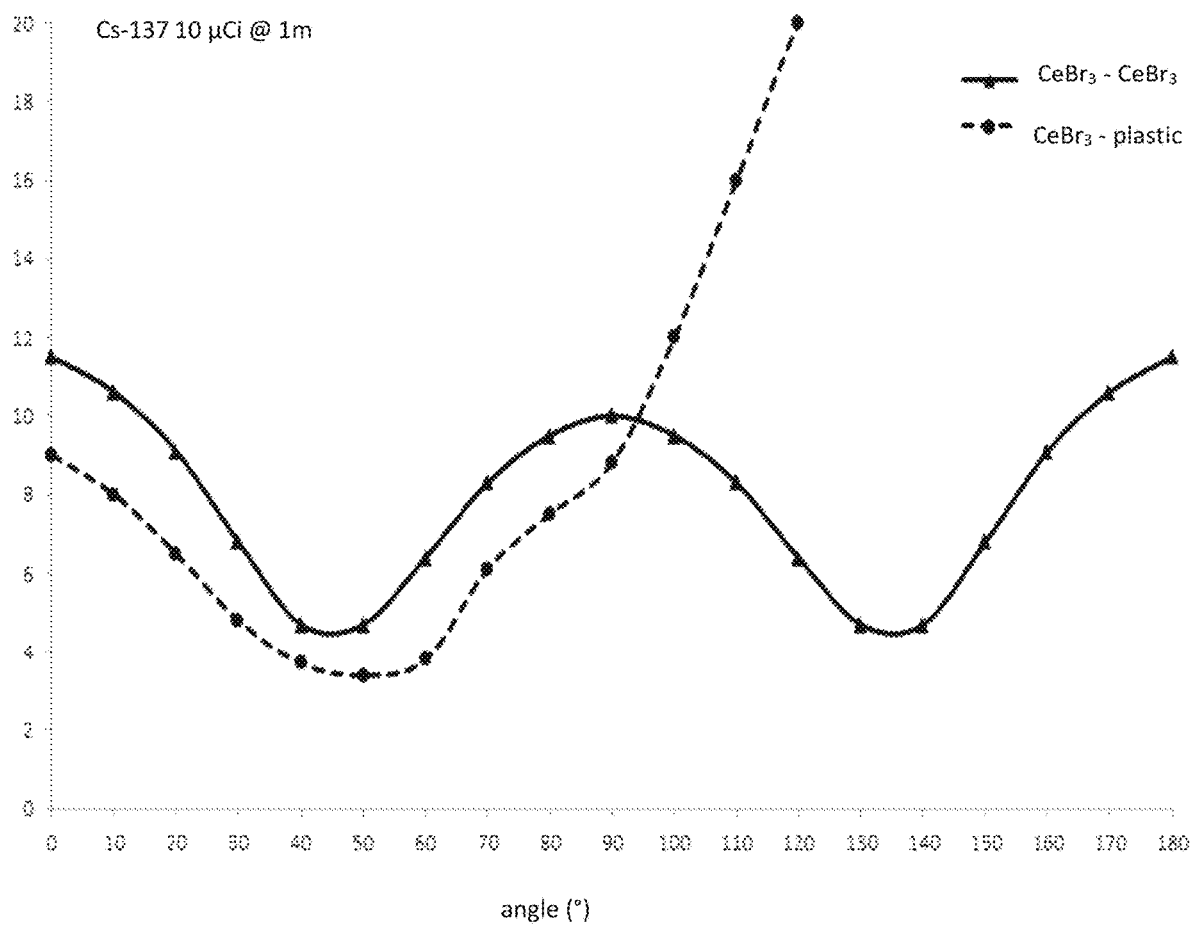
FIG. 19 is a diagram with measurement results for the two-detector arrangement for direction measurement of a Cs-137 source shown in FIG. 17 according to an embodiment of the imaging detector system according to the invention.

FIG. 19 shows measurement results for the two-detector-arrangement shown in FIG. 17 for direction measurement of a Cs-137 source. The minimum measurement time for an accuracy of the angle of ±10° is illustrated as a function of the angle of incidence, measured in two detector variants with a cerbromide-cerbromide and a cerbromide-plastic detector pair. The local dose rate of the Cs-137 source (10 μCi) was 0.03 μSv/h at the measurement point.

In the following, various imaging detector systems are described in detail in concrete embodiments. Examples of these are explained in the accompanying drawings. The detector systems presented here have been developed for the direction measurement of radiation sources in the far field. The detector systems use radiation detectors without local information concerning the interaction point. The image reconstruction methods are suitable for 2-dimensional and for the 3-dimensional direction measurement with stationary or almost stationary measurement conditions.

At first, various embodiments for 3-dimensional detector topologies will be presented. The detectors of a detector system of type B may be arranged, e. g., at the corner points of a polyhedron (FIGS. 11b and 13). In most cases, the polyhedron preferably will be convex.

With respect to a detector system of type A mixed, the detector shell may also be formed as a polyhedron. Detectors having a low and a high atomic number are distributed heterogeneously over the polyhedron.

Selected corners of a type A mixed system in form of a polyhedron may be occupied with detectors of a high atomic number such that inscribed polyhedrons are created. For example, FIG. 12b shows a cube-shaped detector arrangement of type A mixed. Four cube corners are occupied by detectors of high atomic number. They together form a type B detector system having the shape of a tetrahedron.

Detector systems of type A separated may be designed as polygons or polyhedrons of detectors having a low atomic number. In their interior, there is a group of detectors of high atomic number. The detector system shown in FIG. 11a comprises two inner detectors that are arranged one above the other, around which six ring detectors are grouped. It also is possible that the inner core of detectors having a high atomic number forms a small polyhedron within an outer polyhedron made up from detectors of low atomic number (FIGS. 12a and 12c).

A detector material suitable for imaging detector systems for some embodiments of the system is the scintillator material cerbromide. Having an effective atomic number $Z_{eff}$ of 45.9, it is well suited as an absorbing detector material in unidirectional pairs as well as a scattering and absorbing material in bidirectional pairs, too. Cerbromide crystals have a density of 5.1 g/cm³. Typical values for the energy resolution are lying within the range from 3.8% to 4.2% at 662 keV. With a decay time (1/e) of approximately 20 ns, coincidences may be detected with a time resolution of a few nanoseconds.

In the following, two embodiments for detector pairs will be presented by means of specific material combinations. Each one of the detector pairs shown here respectively comprises a cerbromide crystal. If the cerbromide crystal is combined with a plastic scintillator, a unidirectional detector pair is created. By forming pairs of respectively two cerbromide crystals, bidirectional detector pairs are created.

For the dimensioning of the detectors, the interaction probabilities of the detector materials in the energy range, in which the device is to be used, has to be taken into consideration. For the gamma energies of Cs-137 and Co-60, the corresponding probabilities for cerbromide crystals and plastic scintillators are listed in Tab. 2 and 3. Detector planes with thicknesses of 1", 2", or 3" and infinite lateral extension have been considered. The specifications for simple scattering are referred to events, in which the gamma radiation has been scattered one time, before leaving the scintillator through the front or rear side.

TABLE 2

Cerbromide-plastic detector pair (respectively one plane)

| nuclide | Probability $P_{CSS}$ for single scattering (excluding multiple scatterings) | Probability $P_{PE}$ for photoelectric absorption | Total probability $P_{ges} = P_{CSS} \cdot P_{PE}$ |
|---|---|---|---|
| | 1" plastic | 1" CeBr₃ | |
| Cs-137 | 17% | 34% | 6% |
| Co-60 | 14% | 18% | 3% |
| | 2" plastic | 2" CeBr₃ | |
| Cs-137 | 23% | 62% | 14% |
| Co-60 | 20% | 42% | 8% |
| | 3" plastic | 3" CeBr₃ | |
| Cs-137 | 24% | 79% | 19% |
| Co-60 | 22% | 60% | 13% |

Table 2 interaction probabilities for single scattering in a detector plane of aplastic scintillator and for photoelectric absorption in a detector plane from crystalline CeBr₃ depending on the nuclide energy and the scintillator thickness.

TABLE 3

Cerbromide-Cerbromide detector pair (respectively one plane)

| Nuclide | Probability $P_{CSS}$ for single scattering (excluding multiple scatterings) | Probability $P_{PE}$ for photoelectric absorption | Total probability $P_{ges} = 2 \cdot P_{CSS} \cdot P_{PE}$ |
|---|---|---|---|
| | 1" CeBr₃ | 1" CeBr₃ | |
| Cs-137 | 18% | 34% | 12% |
| Co-60 | 18% | 18% | 6% |

TABLE 3-continued

Cerbromide-Cerbromide detector pair (respectively one plane)

| Nuclide | Probability $P_{CSS}$ for single scattering (excluding multiple scatterings) | Probability $P_{PE}$ for photoelectric absorption | Total probability $P_{ges} = 2 \cdot P_{CSS} \cdot P_{PE}$ |
|---|---|---|---|
| | 2" CeBr$_3$ | 2" CeBr$_3$ | |
| Cs-137 | 13% | 62% | 16% |
| Co-60 | 16% | 42% | 13% |
| | 3" CeBr$_3$ | 3" CeBr$_3$ | |
| Cs-137 | 8% | 79% | 13% |
| Co-60 | 13% | 60% | 16% |

Table 3 interaction probabilities for single scattering and for photoelectric absorption in one detector plane of crystalline CeBr$_3$ respectively depending on the nuclide energy and on the scintillator thickness.

With a gamma energy of 662 keV, for cerbromide-cerbromide detector pairs the optimum scintillator thickness for single scattering lies within the range from 20 to 30 mm at 1332 keV, wherein the optimum is reached between 30 to 40 mm. For larger crystals, multiple scatterings increase, which do not contribute to usable direction information. The best values for the total probability $P_{ges}^{max}$ in the energy range of Cs-137 and Co-60 are reached at 2" to 3" scintillator thicknesses.

For energies below 300 keV, the cerbromide-plastic combination is—independent of the thickness—always superior to the cerbromide-cerbromide combination.

Above of 300 keV, the situation is a little bit more complex. FIG. 16a illustrates that for a scintillator thickness of 1", the total probability $P_{ges}$ for cerbromide-cerbromide pairs is higher than the one of cerbromide-plastic pairs above of 350 keV. A similar trend can also be observed at a 2" scintillator thickness (FIG. 16b). At a scintillator thickness from 1" to 2", higher total probabilities can be achieved in a wide energy range for cerbromide-cerbromide pairs than for pairs of cerbromide and plastic. Detector systems, which exclusively consist of cerbromide detectors, therefore, are predestined for small compact handheld devices.

For a good total probability in the energy range from 100 keV to 1500 keV, it is advantageous to combine the respective advantages of the uni- and bidirectional detections with each other. This may be achieved best with a type A system made up by cerbromide and plastic detectors, which has a high proportion of bidirectional detector pairs. For an optimum design for the energy range from 100 keV to 1500 keV, cerbromide and plastic detectors having a size from 2" to 3" are suitable.

After various variants for the spatial detector arrangement and the detector materials have been dealt with, in the following, various measurements are presented, which may be performed by means of certain embodiments of the imaging detector system according to the invention.

In its most simple design, embodiments of the imaging detector system according to the invention can consist of two radiation detectors. Such a detector system has been set up with two 3"×3" cerbromide scintillation detectors in a distance of 18 cm (measured from center to center) (FIG. 17). Further, a second detector system has been used, which comprises a 3"×3" cerbromide detector and a 3"×3" plastic (EJ-200) detector. The second detector system has served as a basis for comparison, in order to be able to compare the bidirectional cerbromide-cerbromide detector pair to the unidirectional cerbromide-plastic detector pair.

All scintillators have been cylindrically shaped and had a size of respectively 3"×3". Each scintillation detector has been equipped with a photomultiplier and a high-voltage supply. Cerbromide and plastic scintillation detectors generate short fast pulses with large amplitudes, which may be connected to a digitizer directly without any preamplifier. The digitizer module comprised one A/D converter per detector respectively, with subsequent FPGA for digitalization of the signals, as well as a readout controller FPGA for fast analysis. The digitizer has had a sufficiently high sampling rate of 500 MS/s such that the signal path of the cerbromide and plastic detectors could be integrated digitally. The processed data have been read out from a PC by means of an USB, have been further processed by means of a measurement technology software, and have been displayed for the user.

The field of vision of the two-detector-arrangement is delimited to a semicircle. It is to be noted that such a system is not able to determine on which side of the connection axis a radiation source is located.

The data acquisition system has been configured according to the scheme of FIG. 3b. The projection data $\underline{p}(\underline{y})$ has been acquired as a histogram with the functional value $\sigma(E_1, E_2)$ of eq. (4). The system matrixes $\underline{H}$ have been determined experimentally for both detector systems by setting up a radiation source under different angles of incidence with respect to the axis of the detector pair. System matrixes have been created for respectively two radio nuclides (Co-60 and Cs-137). The image reconstruction has been carried out by means of the Maximum Likelihood Expectation Maximization Method (MLEM). The result of the image reconstruction was a direction distribution $\underline{f}(\underline{x})$ over the azimuth angle $\underline{x}$ in an angle range from 0° to 180°.

The measurements have been carried out by means of a Co-60 (10 µCi) and a Cs-137 source (10 µCi) in one meter distance respectively. The measurements respectively have been run for one minute. At each point of time t, an estimated value for the direction of the source has been calculated at the maximum of the MLEM function $\underline{f}(\underline{x})$. For data acquisition, 20 measurements have been carried out in total for each angle of incidence of the radiation source. For each angle of incidence from 0° to 180°, the minimum measurement time $t_{90}$ has been determined in order to determine the angle of incidence with an accuracy of ±10° at 90% confidence level. $t_{90}$ is defined as that time, from which on at least 18 of the total of 20 measurements are correct, i. e., are lying in an interval of ±10° around the true value. FIGS. 18 and 19 show the $t_{90}$ measurement times for the cerbromide-cerbromide detector pair compared to the cerbromide-plastic detector pair over the angle range from 0° to 180°.

The bidirectional measurement by means of the cerbromide-cerbromide detector pair is characterized by its large field of vision, which covers the entire angle range from 0° to 180°. For Co-60, all $t_{90}$ measurement times of the cerbromide-cerbromide detector pair were below 8 s and for Cs-137 below 12 s.

On the other hand, the field of vision of the unidirectional cerbromide-plastic detector pair is actually delimited to about 100°. The direction measurement is achieved fast and reliably on the side of the plastic detector, on the other side of the cerbromide detector, in contrast, the direction measurement is only possible at the very late point of time or even is not possible at all.

Within the field of vision, which is delimited to about 100° for the cerbromide-plastic detector pair, the $t_{90}$ measurement times of both detector pairs have a similar magnitude. Only slight differences have been determined between the bidirectional cerbormide-cerbromide and the unidirectional cerbromide-plastic detector pairs.

The measurements reveal that bidirectional cerbromide-cerbromide detector pairs are very well suited for direction measurement. With respect to a quantitative evaluation, cerbromide-cerbromide detector pairs yield similarly good results as cerbromide-plastic detector pairs, their measurement range is even larger because the entire angle range from 0° to 180° can be measured.

Statements for 1-dimensional detector systems may be deduced from the measurement results. Here, an embodiment for a type A mixed system will be considered, in which a cerbromide and a plastic detector are respectively arranged in a row, one behind the other. The detector row is able to measure the entire angle range from 0° to 180°, because in the row, there are unidirectional detector pairs formed from respectively one cerbormide and one plastic detector, which have the plastic detector arranged on the left side as well as on the right side. In another embodiment for a type B system, the entire row consists of cerbromide detectors. Each pair in a cerbromide detector row covers the entire angle range from 0° to 180°.

Besides the detector materials cerbromide and plastic from the system variants presented here, a plurality of further detector materials is known, which may be used for embodiments of the invention. In particular, semiconductor and scintillator materials may also be combined with each other. A frequently used construction principle in detector systems of type A is the combination of a silicon pad or strip detector with a scintillation detector, as NaI, CsI, $CeBr_3$ or $LaBr_3$.

Various designs for the construction of radiation detectors are known in the field of detector engineering. For each detector design, there are, in turn, electronics components available that are adjusted to the respective design. Specialists in this technical field are able to optimize the experimental setup for certain detector requirements without any difficulties.

For the image reconstruction, there are a plurality of methods available. Basically, all statistical image reconstruction methods of emission tomography are suitable within the meaning of the invention for the imaging detector system according to the invention. The embodiments described above use the Maximum Likelihood Expectation Maximization Method (MLEM), which belongs to the group of the EM image reconstruction methods. Other known methods from the group of EM methods are, for example
- Ordered Subset Expectation Maximization (OSEM)
- List Mode—Maximum Likelihood Expectation Maximization (LM-MLEM)
- List Mode—Ordered Subset Expectation Maximization (LM-OSEM) algorithm
- EM methods with penalty functions, e.g. for sparse solutions
- Generalized Expectation Maximization (GEM)
- Space-Alternating Generalized EM (SAGE)

Moreover, further statistical methods are known in the field of emission tomography, which represent method embodiments suitable for the imaging detector system. These comprise:
- Algebraic reconstruction technique (ART)
- Maximum A Posterior algorithm (MAP)
- Maximum Entropy algorithm (ME)
- Origin Ensemble algorithm (OE)

Embodiments of the imaging detector system together with embodiments of the method described here meets the requirements, which are posed to the direction measurement, detection and mapping of radiation sources in ABC and radiation protection. Embodiments of invention can enrich the field of radiation detection with directional resolution by various aspects, amongst others, by the following contributions:
- field of vision over the entire $4\pi$ spatial angle
- fast direction determination
- typical angular resolution at a dose rate of the source of 0.5 μSv/h
  - after 2 s: better than 10°
  - after 3 s: better than 5°
- recognition of multiple sources of similar and different nuclides with separate direction and intensity measurement
- compact device shapes with few detectors:
  - ≥2 detectors for two-dimensional detection in the plane
  - ≥3 detectors for three-dimensional detection in a half space
  - ≥4 detectors for three-dimensional detection with $4\pi$ spatial angle
- setups, which use only one detector material or several materials in geometrical arrangements that can be flexibly designed
- simple and fast algorithms, which yield results in real-time
- device supports detection and mapping of radiation sources
- various usage options: stationary and mobile, with one or more devices
- motion tracking and tracking of moving radiation sources possible Moreover, the imaging detector system can also be suitable for applications in nuclear medicine. Embodiments of the invention can open various new possibilities in medical imaging by means of gamma radiation, amongst others, by the following contributions:
- highly efficient SPECT scanners without collimators on the basis of the Compton effect
- SPECT scanners for gamma radiation in the energy range >200 keV
- reduction of exposure to radiation for the patients
- setups, which use only one detector material for several materials in geometrical arrangements that can be flexibly designed
- use of PET scanners as SPECT and PET/SPECT hybrid scanners
- algorithms from emission tomography can be used
- new imaging techniques for radiopharmaceuticals, which are single photon and positron emitters
- compact designs for SPECT and PET/SPECT hybrid sensors in decentral diagnostics A further use option for embodiments of the imaging detector system is in astronomy using gamma radiation. The invention supports the construction of new Compton telescopes as imaging detector systems according to the invention with improved sensitivity at the same material input.

The present invention has been described by means of some specific embodiments of the devices and methods. Persons skilled in the art in the field of radiation detection, of course, are able to modify these embodiments without departing from the principles and the spirit of the invention, the scope of protection of which is defined in the claims and its equivalents.

The invention claimed is:

1. A device for generating one or more images of a source distribution of a gamma radiation field in a near field and a far field, comprising:
   a detector system comprising a group of several synchronized detectors for detection of radiation, wherein at least one detector material has an atomic number of $Z_{eff}>30$ and all detectors measure energies E and interaction points $\underline{d}$, which occur in interactions of radiation with detector materials of the detectors, wherein the detector materials are segmented virtually and physically into voxels;
   a system electronics configured to register one or more coincidence events in response to interactions occurring in at least two detector voxels from a list of defined voxel pairs simultaneously; wherein a list of defined voxel pairs comprises all pairs which are formed in combination from all the detector voxels, and the defined voxel pairs comprise at least one detector voxel made from the detector material having the atomic number of $Z_{eff}>30$;
   a data acquisition system configured to store the measurement data of the one or more coincidence events and determine a ranking for both detector voxels involved in each coincidence event, which defines a first detector voxel and a second detector voxel; wherein in each defined voxel pair, the voxel having the lower atomic number receives the number 1, and that one having the higher atomic number receives the number 2; wherein in case both detector voxels of a pair should have the same atomic number, the indication of 1 and 2, respectively, is made arbitrarily,
   the data acquisition system configured to sort the energies ($E_1$, $E_2$) measured in the coincidence events and the interaction points ($\underline{d}_1$, $\underline{d}_2$) corresponding to their indication 1, 2, and stores them in a chronological list together with the attributes $\underline{y}=\{\underline{d}_1, E_1, \underline{d}_2, E_2\}$ and the detector time t; and
   an analysis unit connected to the data acquisition system, the analysis unit configured to generate projection data $\underline{p}(\underline{y})$ from the stored measurement data, which are defined as a function of the attributes $\underline{y}=\{\underline{d}_1, E_1, \underline{d}_2, E_2\}$, wherein a function $\sigma(E_1,E_2)$ is applied, which is dependent on two energy values ($E_1$, $E_2$), and this function $\sigma(E_1,E_2)$ when substituting $E_2$ by $C-E_1$ is traceable to a function $\sigma(E_1)$, which over an entire interval [0, C] is clearly defined, constant, and monotonous, wherein C is a constant, which represents a radiation energy $C=E_1+E_2$; and
   the analysis unit is configured to perform an image reconstruction that reconstructs one or more images $\underline{f}(\underline{x})$ of the source distribution of the radiation field from the projection data $\underline{p}(\underline{y})$.

2. The device according to claim 1, wherein the detector system detects radiation fields, which have a discrete and/or a continuous distribution of radiation, wherein the detector system is located in a geometrical near field and/or far field of the radiation field;
   and/or that the radiation sources emit gamma, electron, positron, proton, ion and/or neutron radiation;
   and/or that the radiation originates from the radioactive decay of one or more radio nuclides;
   and/or that the radiation is the prompt gamma radiation, which is generated during the absorption of proton or ion radiation in target materials;
   and/or that the radiation is of low intensity, as for example, in astronomy.

3. The device of claim 2, characterized in that the detectors comprise:
   a scintillator with a photodetector and/or a semiconductor material;
   and/or that the scintillator comprises a pure or a doped material from the group of PVT, anthracene, stilbene, p-terphenyl, $CaF_2$, $BaF_2$, NaI, $CeBr_3$, $LaBr_3$, $LaCl_3$, $La(Br_xCl_{1-x})_3$, CsI, $SrI_2$, CLYC, CLBC, CLCB, CLLB, BGO, LSO, LYSO, GAGG, YAP and/or YAG;
   and/or that the scintillator is present as a monolithic block or as pixelated scintillator module;
   and/or that the photodetector is a photomultiplier (PMT), a photomultiplier with location resolution (PSPMT), a silicon photomultiplier (SiPM), a silicon photomultiplier with location resolution (PS-SiPM) and/or a silicon photodiode;
   and/or that the semiconductor material comprises a material from the group of Si, Ge, GaAs, CdTe and/or CdZnTe;
   and/or that the semiconductor material has a planar or coaxial geometry and/or is available with segmented or unsegmented contacts;
   and/or that the scintillator and the semiconductor material, respectively, are subdivided virtually or physically into an arbitrary integer number of $\geq 1$ voxels.

4. The device according to claim 3, wherein:
   the system electronics uses analog and/or digital electronic components;
   and/or that the analog electronic components comprise a combination of various modules, which comprise a high-voltage supply, a preamplifier, an amplifier, a pulse shaper, a charge integrator, a pulse height analyzer, a multichannel analyzer (MCA) and/or a coincidence circuit;
   and/or that the digital electronic components comprise a combination of various hardware and software components, which comprise a high-voltage supply, an A/D converter per detector voxel, a Field Programmable Gate Array (FPGA), a storage medium, a digital signal processor, and/or the analysis software.

5. The device of claim 4, wherein:
   the interaction points ($\underline{d}_1$, $\underline{d}_2$) are determined on the basis of the location resolving properties of the detectors, and/or on the basis of the available segmentation of the detectors;
   and/or that the interaction points ($\underline{d}_1$, $\underline{d}_2$) are defined as the spatial centers of a first and a second detector voxel of the detector voxels involved in a coincidence event;
   and/or that the functional value $\sigma(E_1,E_2)$ is defined according to:

$$\sigma(E_1,E_2)=(E_2-E_1)/(E_1+E_2)$$

6. The device of claim 1, wherein:
   the analysis unit reconstructs the radiation field using projection data $\underline{p}(\underline{y})$ which is defined as a function of the attributes $\underline{y}=\{\underline{d}_1, E_1, \underline{d}_2, E_2\}$;
   and/or that for each element of $\underline{p}$, a number of coincidence events is determined, which occur at a respective combination of a particular first detector voxel with a particular second detector voxel at a particular functional value $\sigma(E_1,E_2)$;
   and/or that for each element of $\underline{p}$, a number of coincidence events is determined, which occurs at a respective combination of a particular first detection location $\underline{d}_1$ with a particular second detection location $\underline{d}_2$ at a particular functional value $\sigma(E_1,E_2)$.

7. The device of claim 1, wherein a selection condition for coincidence events is applied with respect to the energy sum $E_1+E_2$ of the energies detected in both detector voxels of a pair;

and/or that separate projection data $\underline{p}(\underline{y})$ is created for each detected radio nuclide;

and/or that the analysis unit is configured to calculate a separate image $\underline{f}(\underline{x})$ for each radio nuclide.

8. The device of claim 1, wherein:

the images $\underline{f}(\underline{x})$ represent an activity density, a flux density, and a dose rate density, respectively;

and/or the images $\underline{f}(\underline{x})$ are tomographic sectional images of an activity distribution of radio nuclides (for example, also radiopharmaceuticals).

9. The device of claim 1, wherein all the detectors have a same design, or that at least two of the detectors have a design different from each other.

10. The device according to claim 1, wherein:

the detector system comprises at least four detector voxels in a substantially three-dimensional arrangement, and has a field of vision with a $4\pi$ spatial angle;

or that the detector system comprises at least three detector voxels in a substantially two-dimensional arrangement, and has a hemispherical field of vision with a a $2\pi$ spatial angle;

or that the detector system comprises at least three detector voxels in a substantially two-dimensional arrangement, and has a 360° field of vision in the plane of the radiation detectors;

or that the detector system comprises at least two detector voxels in a one-dimensional detector row, and has a 180° field of vision from −90° to +90° perpendicular to the detector row.

11. The device of claim 1, wherein the detector system comprises a first group of detectors/voxels having an atomic number of $Z_{\mathit{eff}}>30$, which have high probabilities for photoelectric absorption in the energy range from 100 keV to 3 MeV.

12. The device of claim 10, also comprising a second group of detectors/voxels having an atomic number of $Z_{\mathit{eff}} \leq 30$, which have high probabilities for Compton radiation in the energy range from 100 keV to 3 MeV.

13. The device of claim 12, wherein:

data is acquired from all detector pairs/voxel pairs, which may be formed in combination from the quantity of all detectors/voxels, wherein such detector pairs/voxel pairs are excluded, in which both detectors/voxels belong to the second group having an atomic number of $Z_{\mathit{eff}} \leq 30$;

and/or the mixed detector pairs/voxel pairs, which comprise the respectively one detector/voxel from the first group and one detector/voxel from the second group, are unidirectional, wherein the radiation predominantly is scattered in one direction;

and/or the detector pairs/voxel pairs of the first group having an atomic number of $Z_{\mathit{eff}}>30$ are bidirectional, wherein the radiation is scattered in both directions with a similar intensity.

14. The device of claim 1, wherein:

an entirety of the detectors/voxels, which are comprised in the detector system, comprises a first homogeneous or heterogeneous annular, tubular, cylindrical, spherical, and/or polyhedral shape;

and/or that the entirety of the detectors/voxels, which are comprised in the detector system, in addition to the first shape, comprise a second homogeneous or heterogeneous annular, tubular art, cylindrical, spherical, and/or polyhedral shape, and wherein the second shape is inscribed within the first shape, or wherein the second shape is arranged in an internal region, which is enclosed by the first shape as an outer shell;

and/or wherein the first and/or the second shape are arranged around one or more central detectors.

15. The device of claim 1, wherein a part of the system or the entire system is configured as a locating device for radiation sources, as a Compton camera, as a Compton telescope, as a SPECT scanner, as a PET/SPECT hybrid scanner, as a SPECT sensor, and/or as a PET/SPECT hybrid sensor.

16. A method for the use of a device for generating one or more images of a source distribution of a gamma radiation field a, wherein the detector materials are segmented into voxels virtually and physically, wherein the method uses unidirectional and bidirectional Compton scattering processes and has a system matrix $\underline{H}$, a defined functional value $\sigma(E_1, E_2)$ and a list of defined voxel pairs, and is adapted for the acquisition of projection data $\underline{p}(\underline{y})$ of the measurement values and for the calculation of image data $\underline{f}(\underline{x})$, the method comprising:

creating a list with defined voxel pairs, wherein the defined voxel pairs comprise all pairs, which may be formed in combination from the quantity of the detector voxels, and wherein each pair comprises at least one detector voxel made from a material having an atomic number of $Z_{\mathit{eff}}>30$;

interconnecting all detectors/voxels in a coincidence circuit such that coincidence events are acquired in all defined voxel pairs;

indicating the two detector voxels of each voxel pair with the numbers 1 and 2, respectively, wherein the detector voxel having the lower atomic number receives the number 1, and that one having the higher atomic number receives the number 2, wherein if both detectors voxels consist of the same material, the indication is made arbitrarily;

defining a function $\sigma(E_1, E_2)$ which is calculated from to energy values $(E_1, E_2)$, wherein such functions $\sigma(E_1, E_2)$ are allowable, which are traceable when substituting $E_2$ by $C-E_1$ to a function $\sigma(E_1)$, which for the entire interval $[0, C]$ is clearly defined, constant, and monotonous; hereby, C is a constant, which represents the radiation energy $C=E_1+E_2$;

acquiring measurement values $\underline{y}=\{\underline{d}_1, E_1, \underline{d}_2, E_2\}$ of coincidence events, if interactions take place in respectively two detector voxels of all defined voxel pairs, wherein the measurement values originate from a radiation near field or far field, and the measurement values are the energies $(E_1, E_2)$ measured in the detector voxels and the interaction points $(\underline{d}_1, \underline{d}_2)$, associating coincidence events $\underline{y}=\{\underline{d}_1, E_1, \underline{d}_2, E_2\}$ with a first detector voxel/detection location $\underline{d}_1$ and a second detector voxel/detection location $\underline{d}_2$;

calculating the functional value $\sigma(E_1, E_2)$ from two energy values $(E_1, E_2)$ per coincidence event;

acquiring the coincidence events corresponding to their first two detector voxel $\underline{d}_1$, their second detector voxel $\underline{d}_2$ and their $\sigma(E_1, E_2)$ value in an element of the projection data $\underline{p}(\underline{y})$, wherein separate projection data $\underline{p}(\underline{y})$ is required for each radio nuclide;

calculating one or more images $\underline{f}(\underline{x})$ from the projection data $\underline{p}(\underline{y})$ by means of a statistical image reconstruction method of emission tomography using the system matrix $\underline{H}$, wherein a separate image $\underline{f}(\underline{x})$ is calculated for each radio nuclide; wherein the images $\underline{f}(\underline{x})$ represent an activity distribution in a source volume or a flux density distribution over the directions of incidence.

17. The method of claim 16, comprising at least one of:

calibrating the signals of all detector voxels as absorbed radiation energy E;

determining a suitable coordinate system;

subdividing the measurement area for the functional value $\sigma(E_1,E_2)$ into equidistant measurement value channels;

creating one or more projection data sets $\underline{p}(\underline{y})$, which acquire the numbers of coincidence events, which are counted for a respective combination of a particular first detector voxel $\underline{d}_1$ with a particular second detector voxel $\underline{d}_2$ at a particular functional value $\sigma(E_1, E_2)$, wherein a separate projection data set $\underline{p}(\underline{y})$ is created for each radio nuclide;

creating one or more system matrixes $\underline{H}$ for each radio nuclide to be detected;

creating and validating the system matrixes $\underline{H}$ by means of measurements using the detector system, or by means of Monte Carlo simulations or by means of a theoretical model; and transferring all system matrixes $\underline{H}$ to an algorithm of the image reconstruction, which processes the projection data $\underline{p}(\underline{y})$ and calculates the images $\underline{f}(\underline{x})$.

\* \* \* \* \*

UNITED STATES PATENT AND TRADEMARK OFFICE
CERTIFICATE OF CORRECTION

| | | |
|---|---|---|
| PATENT NO. | : 11,243,312 B2 | |
| APPLICATION NO. | : 17/101468 | |
| DATED | : February 8, 2022 | |
| INVENTOR(S) | : Sibylle Petrak | |

It is certified that error appears in the above-identified patent and that said Letters Patent is hereby corrected as shown below:

On the Title Page

At item (72) Inventor, change "Hena (DE)" to --Jena (DE)--.

Signed and Sealed this
Fourteenth Day of March, 2023

Katherine Kelly Vidal
*Director of the United States Patent and Trademark Office*